(12) United States Patent
Ehrenfels et al.

(10) Patent No.: US 7,140,527 B2
(45) Date of Patent: *Nov. 28, 2006

(54) SURGICAL FASTENER APPLYING APPARATUS

(75) Inventors: Karl H. Ehrenfels, Cheshire, CT (US); David Ivanko, Fairfield, CT (US); Randolph F. Lehn, Stratford, CT (US); Roberto Pedros, Seymour, CT (US); Csaba L. Rethy, Fairfield, CT (US); Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/292,736

(22) Filed: Dec. 2, 2005

(65) Prior Publication Data

US 2006/0081678 A1    Apr. 20, 2006

Related U.S. Application Data

(62) Division of application No. 10/399,071, filed as application No. PCT/US01/32213 on Oct. 15, 2001, now Pat. No. 7,055,730.

(60) Provisional application No. 60/240,461, filed on Oct. 13, 2000.

(51) Int. Cl.
*A61B 17/072*    (2006.01)
*A61B 17/064*    (2006.01)

(52) U.S. Cl. .................. 227/175.1; 227/19; 227/176.1; 227/180.1

(58) Field of Classification Search .................. 227/19, 227/175.4, 178.1, 177.1, 180.1, 176.1, 175.2, 227/175.3, 175.1
See application file for complete search history.

(56) References Cited

U.S. PATENT DOCUMENTS 3,144,654 A    8/1964    Rudolph et al.

(Continued)

FOREIGN PATENT DOCUMENTS

EP    0 514 185    11/1982

(Continued)

OTHER PUBLICATIONS

International Search Report for PCT/US01/32213.

(Continued)

*Primary Examiner*—Rinaldi I. Rada
*Assistant Examiner*—Nathaniel Chukwurah

(57) ABSTRACT

An improved surgical fastener applying apparatus includes a cartridge half-section and an anvil half-section with the cartridge and anvil half-sections being relatively movable from an unclamped position to a fully clamped position. The apparatus includes a replaceable staple cartridge assembly having a plurality of surgical staples and a pivotably mounted safety lock-out. The safety lock-out is pivotable between an initial position in which a relative movement of the cartridge and anvil half-sections to the fully clamped position is permitted and a blocking position in which a relative movement of the cartridge and anvil half-sections to return them to their fully clamped position after the plurality of staples have been at least partially fired is prevented. The apparatus further includes a pivotably mounted firing lever for moving a pair of camming surfaces longitudinally. In addition, each of the presently disclosed cartridge and anvil half-sections of the fastener applying apparatus includes a clamping lever, which clamping levers are configured and adapted to enable the applying apparatus to be opened by either one of the cartridge half-section and the anvil half-section.

10 Claims, 30 Drawing Sheets

U.S. PATENT DOCUMENTS

| | | | |
|---|---|---|---|
| 4,244,372 A | 1/1981 | Kapitanov et al. |
| 4,397,311 A | 8/1983 | Kanshin et al. |
| 4,589,582 A | 5/1986 | Bilotti |
| 4,596,351 A | 6/1986 | Fedotov et al. |
| 4,605,001 A | 8/1986 | Rothfuss et al. |
| 4,608,981 A | 9/1986 | Rothfuss et al. |
| 4,633,861 A | 1/1987 | Chow et al. |
| 4,633,874 A | 1/1987 | Chow et al. |
| 4,741,336 A | 5/1988 | Failla et al. |
| 4,805,823 A | 2/1989 | Rothfuss |
| 4,869,415 A | 9/1989 | Fox |
| 4,892,244 A | 1/1990 | Fox et al. |
| 4,955,959 A | 9/1990 | Tompkins et al. |
| 4,991,764 A | 2/1991 | Mericle |
| 5,065,929 A | 11/1991 | Schulze et al. |
| D322,143 S | 12/1991 | Spreckelmeier |
| 5,071,052 A | 12/1991 | Rodak et al. |
| 5,074,454 A | 12/1991 | Peters |
| 5,083,695 A | 1/1992 | Foslien et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,180,092 A | 1/1993 | Crainich |
| 5,188,274 A | 2/1993 | Moeinzadeh et al. |
| 5,263,629 A | 11/1993 | Trumbull et al. |
| RE34,519 E | 1/1994 | Fox et al. |
| 5,275,323 A | 1/1994 | Schulze et al. |
| 5,332,142 A | 7/1994 | Robinson et al. |
| 5,364,003 A | 11/1994 | Williamson, IV |
| 5,395,034 A | 3/1995 | Allen et al. |
| 5,415,334 A | 5/1995 | Williamson, IV |
| 5,415,335 A | 5/1995 | Knodell, Jr. |
| 5,417,361 A | 5/1995 | Williamson, IV |
| 5,445,304 A | 8/1995 | Plyley et al. |
| 5,465,896 A | 11/1995 | Allen et al. |
| 5,485,947 A | 1/1996 | Olson et al. |
| 5,489,058 A | 2/1996 | Plyley et al. |
| 5,562,241 A | 10/1996 | Knodel et al. |
| 5,630,541 A | 5/1997 | Williamson, IV et al. |
| 5,632,432 A | 5/1997 | Schulze et al. |
| 5,651,491 A | 7/1997 | Heaton et al. |
| 5,662,258 A | 9/1997 | Knodel et al. |
| 5,673,842 A | 10/1997 | Bittner et al. |
| 5,678,748 A | 10/1997 | Plyley et al. |
| 5,680,983 A | 10/1997 | Plyley et al. |
| 5,697,542 A | 12/1997 | Knodel et al. |
| 5,718,359 A | 2/1998 | Palmer et al. |
| 5,752,644 A | 5/1998 | Bolanos et al. |
| 5,762,255 A | 6/1998 | Chrisman et al. |
| 5,769,303 A | 6/1998 | Knodel et al. |
| 5,779,132 A | 7/1998 | Knodel et al. |
| 5,785,232 A | 7/1998 | Vidal et al. |
| 5,810,240 A | 9/1998 | Robertson |
| 5,826,776 A | 10/1998 | Schulze et al. |
| 5,871,135 A | 2/1999 | Williamson, IV et al. |
| 5,878,938 A | 3/1999 | Bittner et al. |
| 5,893,506 A | 4/1999 | Powell |
| 5,894,979 A | 4/1999 | Powell |
| 5,911,353 A | 6/1999 | Bolanos et al. |
| 5,915,615 A | 6/1999 | Bauer |
| 5,915,616 A | 6/1999 | Viola et al. |
| 5,919,198 A | 7/1999 | Graves, Jr. et al. |
| 5,941,442 A | 8/1999 | Geiste et al. |
| 5,988,479 A | 11/1999 | Palmer |
| 6,010,054 A | 1/2000 | Johnson et al. |
| 6,024,748 A | 2/2000 | Manzo et al. |
| 6,109,500 A | 8/2000 | Alli et al. |
| 6,131,789 A | 10/2000 | Schulze et al. |
| 7,055,730 B1 * | 6/2006 | Ehrenfels et al. ......... 227/175.4 |

FOREIGN PATENT DOCUMENTS

| | | |
|---|---|---|
| EP | 0 625 335 B1 | 11/1994 |
| EP | 0 639 349 A2 | 2/1995 |
| WO | 02 30297 A2 | 4/2002 |

OTHER PUBLICATIONS

International Search Report for PCT/US02/31963.

* cited by examiner

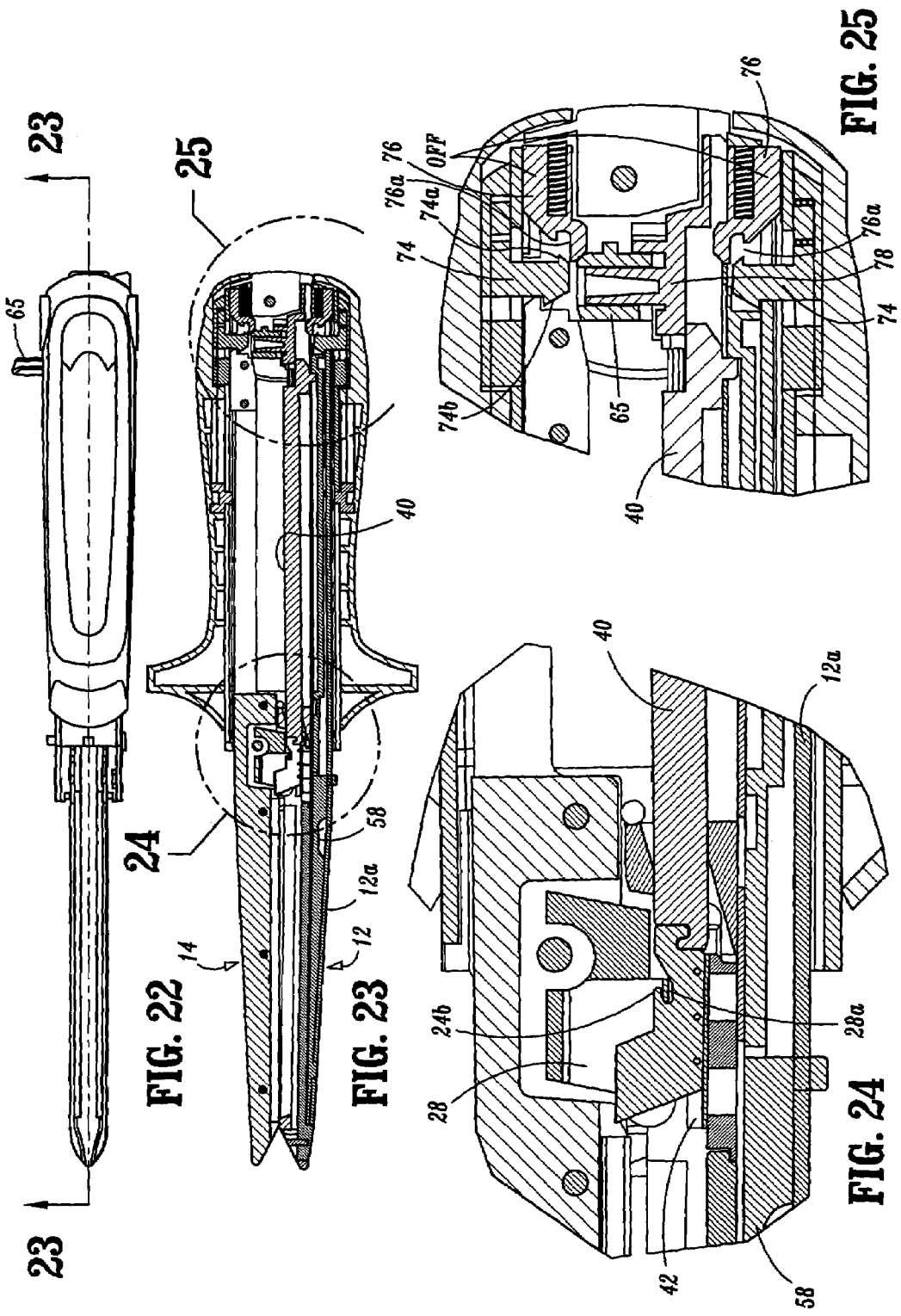

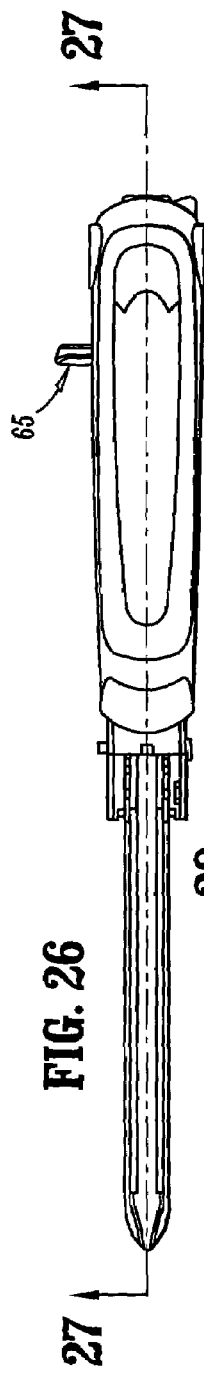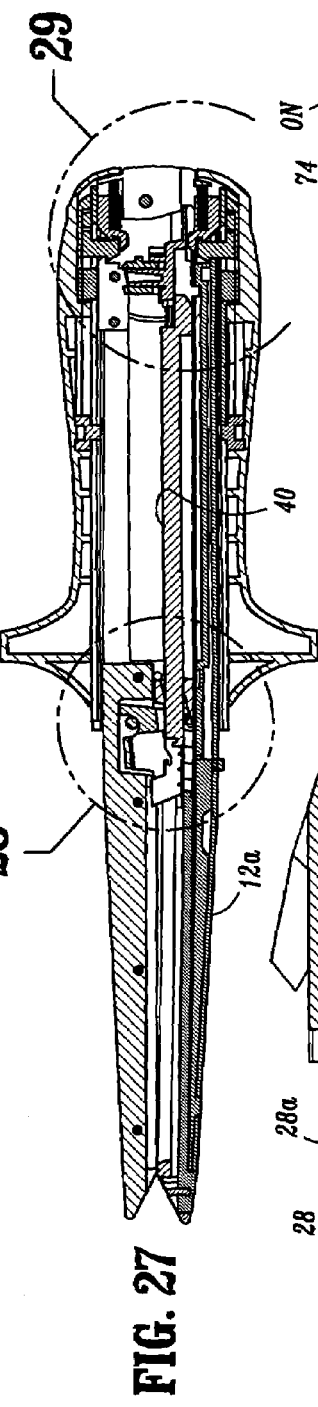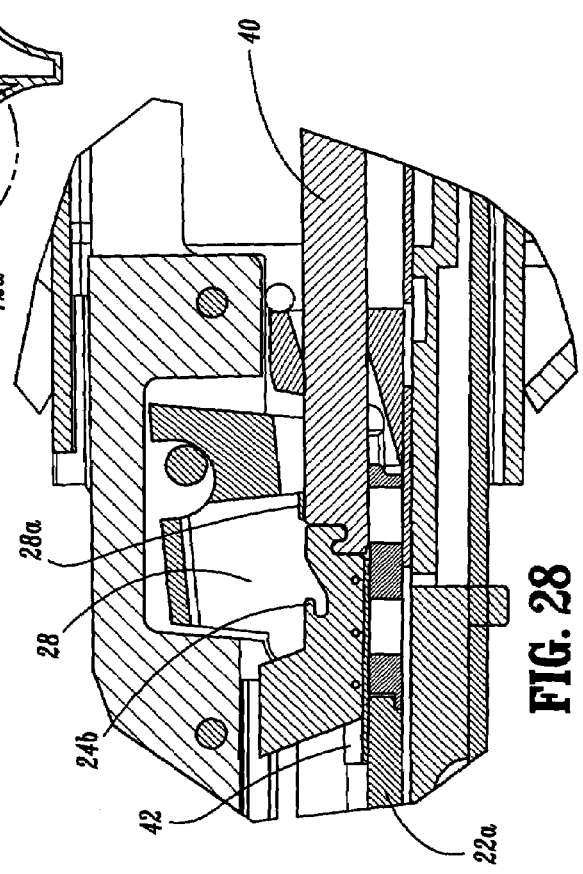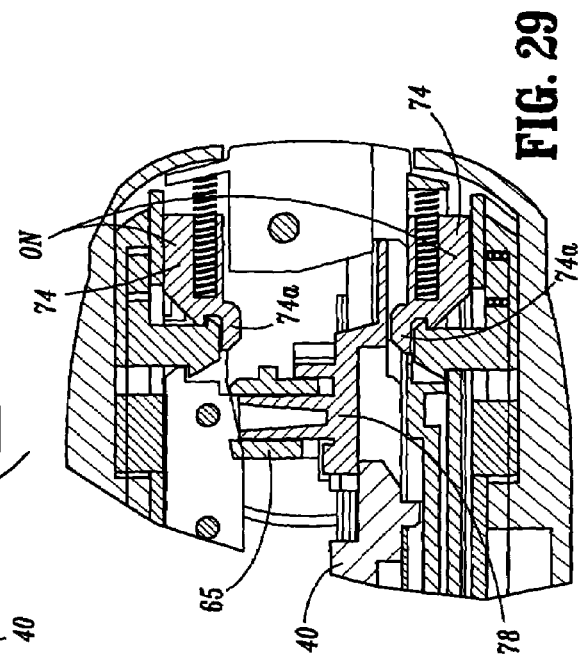
FIG. 26
FIG. 27
FIG. 28
FIG. 29

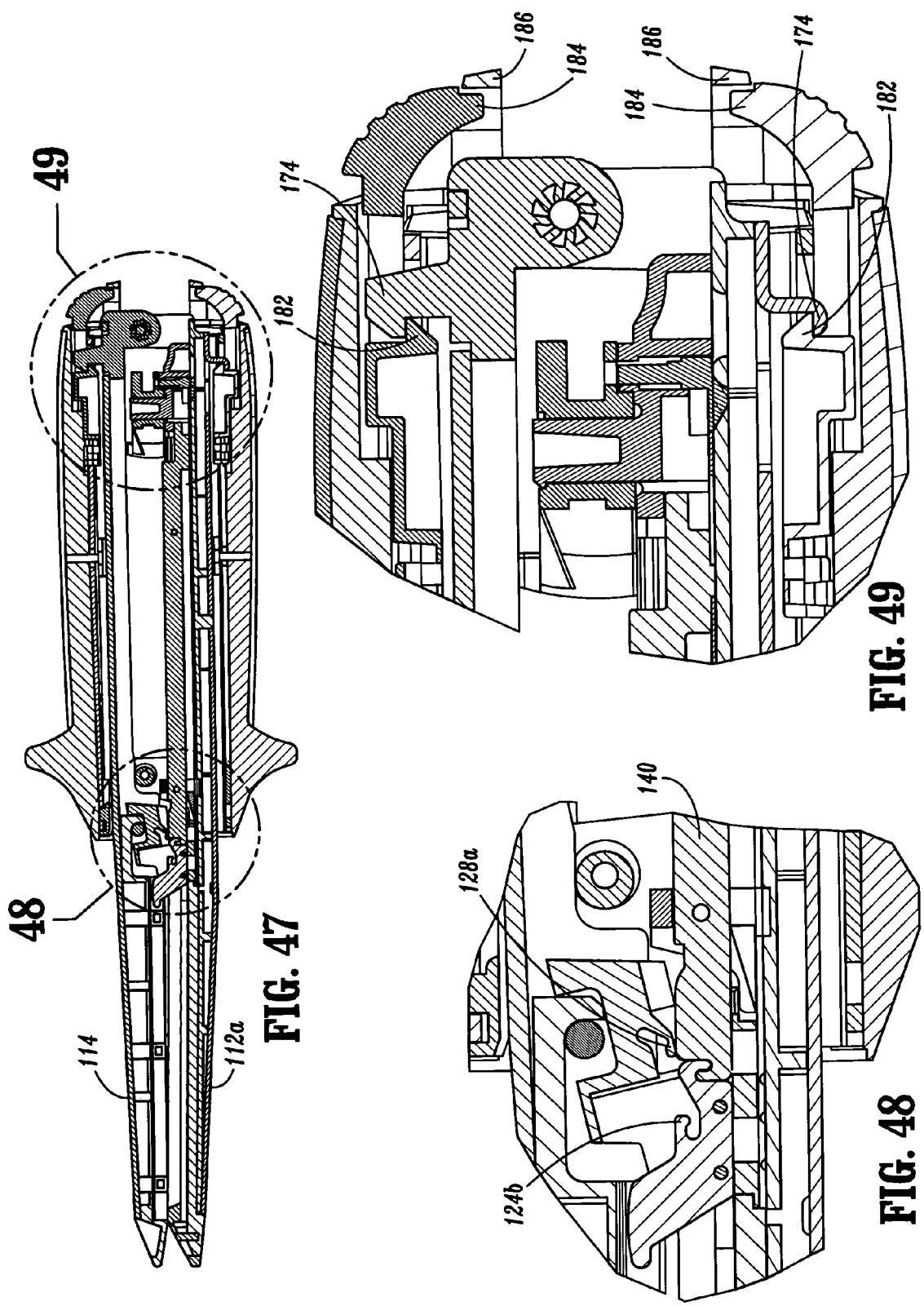

SURGICAL FASTENER APPLYING APPARATUS

CROSS REFERENCE TO RELATED APPLICATIONS

This application is a divisional of U.S. patent application Ser. No. 10/399,071 filed Apr. 10, 2003 now U.S. Pat. No. 7,055,730 which is a national of PCT Ser. No. PCT/US2001/32213 filed Oct. 15, 2001 which claims priority to U.S. Provisional Patent Application Ser. No. 60/240,461 filed Oct. 13, 2000, the disclosures of which are incorporated herein in their entirety by this reference.

BACKGROUND

1. Technical Field

The present disclosure relates to surgical fastener applying apparatus and more particularly to surgical fastener appliers for sequentially applying a plurality of surgical fasteners to body tissue.

2. Discussion of Related Art

Surgical devices wherein tissue is first grasped or clamped between opposing jaw structures and then joined by means of surgical fasteners are well known in the art. In some such instruments a knife is provided to cut the tissue which has been joined by the fasteners. The fasteners are typically in the form of surgical staples however, other surgical fasteners may also be utilized, for example, clips or two part polymeric surgical fasteners.

Instruments for applying surgical fasteners typically include two elongated beam members which are respectively used to capture or clamp tissue therebetween. Typically, one of the beam members carries a disposable cartridge which houses a plurality of staples arranged in at least two lateral rows while the other beam member comprises an anvil which defines a surface for forming the staple legs as the staples are driven from the cartridge. Where two part fasteners are used, this beam member carries the mating part, e.g. the receiver, to the fasteners driven from the cartridge. Generally, the staple formation process is effected by the interaction between a longitudinally moving camming surface and a series of individual staple pusher member. As the camming surface travels longitudinally through the cartridge carrying member, the individual pusher members are biased laterally acting upon the staples to sequentially eject them from the cartridge. A knife may travel with the pusher between the staple rows to longitudinally cut the tissue between the rows of formed staples. Examples of such instruments are disclosed in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples.

SUMMARY

It is an object of the present invention to provide a surgical fastener applying apparatus which apparatus will not fire if a disposable staple cartridge is not properly loaded within the apparatus or is not loaded in the apparatus at all.

It is another object of the present invention to provide a surgical fastener applying apparatus which will not open during the firing stroke of the apparatus.

It is a further object of the present invention surgical fastener applying apparatus which will not accept a completely fired or a partially fired disposable staple cartridge therein.

It is yet another object of the present invention to provide a surgical fastener applying apparatus which will not fire while in an unclamped state.

The presently disclosed apparatus includes a cartridge half-section and an anvil half-section with the cartridge and anvil half-sections being relatively movable from an unclamped position to a fully clamped position. The apparatus further includes a replaceable staple cartridge assembly receivable in the cartridge half-section. The cartridge assembly includes a plurality of surgical staples abutting a plurality of staple pusher members and a pivotably mounted safety lock-out. The safety lock-out is pivotable between an initial position, which permits a relative movement of the cartridge and anvil half-sections to the fully clamped position, and a blocking position, which prevents a relative movement of the cartridge and anvil half-sections from returning to the fully clamped position after the plurality of staples have been at least partially fired. The apparatus further includes a pair of camming surface extensions extending from a cam bar channel and positioned within the cartridge half-section and a pivotably mounted firing lever operatively associated with the pair of camming surfaces to move the pair of camming surfaces longitudinally, thereby sequentially firing the plurality of surgical staples in a direction transverse to a direction of travel of the pair of camming surfaces.

In addition, each of the presently disclosed cartridge and anvil half-sections of the fastener applying apparatus includes a clamping lever, which clamping levers are configured and adapted to enable the applying apparatus to be opened by either one of the cartridge half-section and the anvil half-section. The apparatus including a clamp latch configured and adapted to retain the clamp levers in a clamped orientation and a safety interlock assembly configured and adapted to prevent opening of either of the clamping levers after the firing lever has been moved distally.

BRIEF DESCRIPTION OF THE DRAWINGS

Various embodiments of the presently disclosed surgical fastener applying apparatus will be described herein with reference to the accompanying drawing figures wherein:

FIG. 22 is a plan view looking down on the anvil half-section of the surgical stapler apparatus with a firing lever in the proximal-most position;

FIG. 23 is a cross-sectional view taken along section line 23—23 of FIG. 22;

FIG. 24 is an enlarged view of the indicated area of detail of FIG. 23;

FIG. 25 is an enlarged view of the indicated area of detail of FIG. 23;

FIG. 26 is a plan view similar to FIG. 22, which shows the firing lever advanced distally a short distance;

FIG. 27 is a cross-sectional view taken along section line 27—27 of FIG. 26;

FIG. 28 is an enlarged view of the indicated area of detail of FIG. 27;

FIG. 29 is an enlarged view of the indicated area of detail of FIG. 27;

FIG. 47 is a cross-sectional view of the surgical stapler taken along the longitudinal center line thereof;

FIG. 48 is an enlarged view of the indicated area of detail of FIG. 47;

FIG. 49 is an enlarged view of the indicated area of detail of FIG. 47;

DETAILED DESCRIPTION OF PREFERRED EMBODIMENTS

Figure 1:
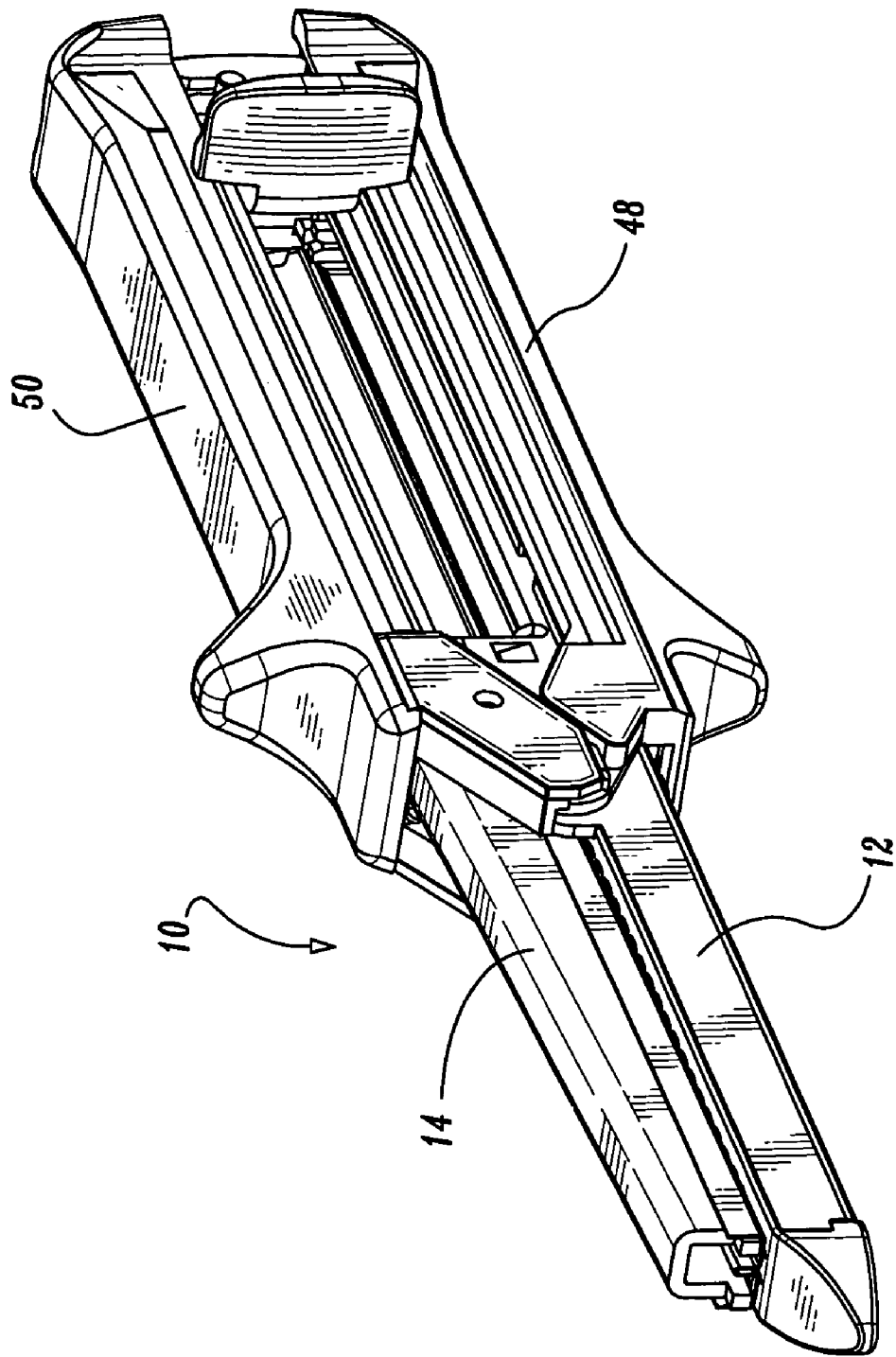
FIG. 1 is a perspective view of one embodiment of a surgical fastener apparatus constructed in accordance with the present disclosure.
Figure 2:
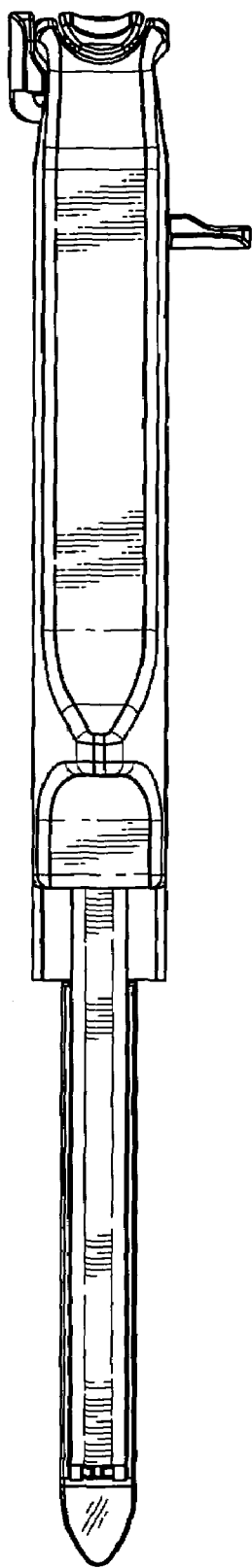
FIG. 2 is a top plan view of the embodiment of FIG. 1.
Figure 3:
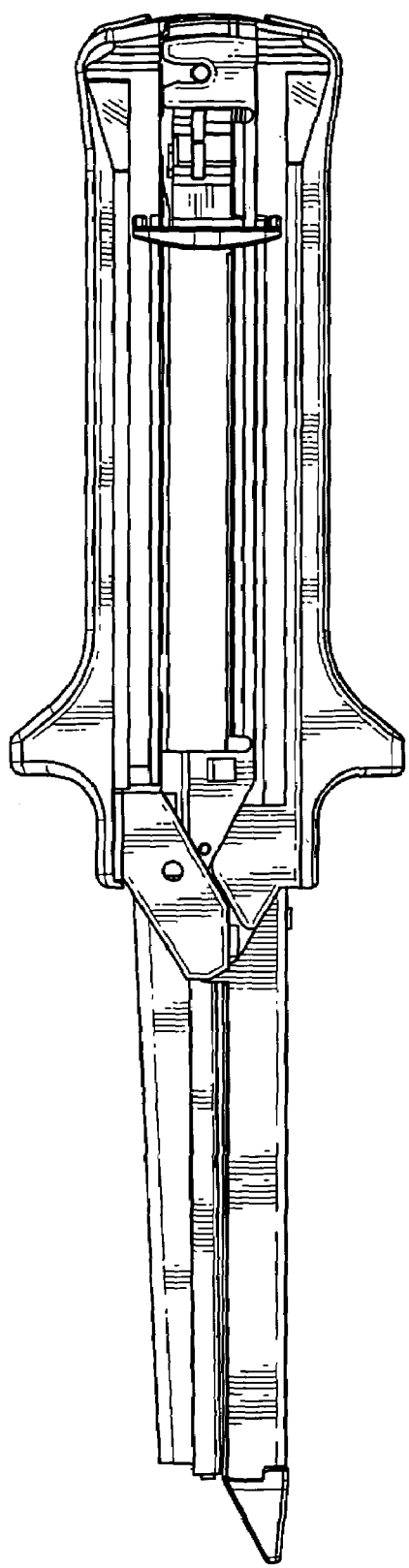
FIG. 3 is a side elevation view of the embodiment of FIG. 1.
Figure 4:
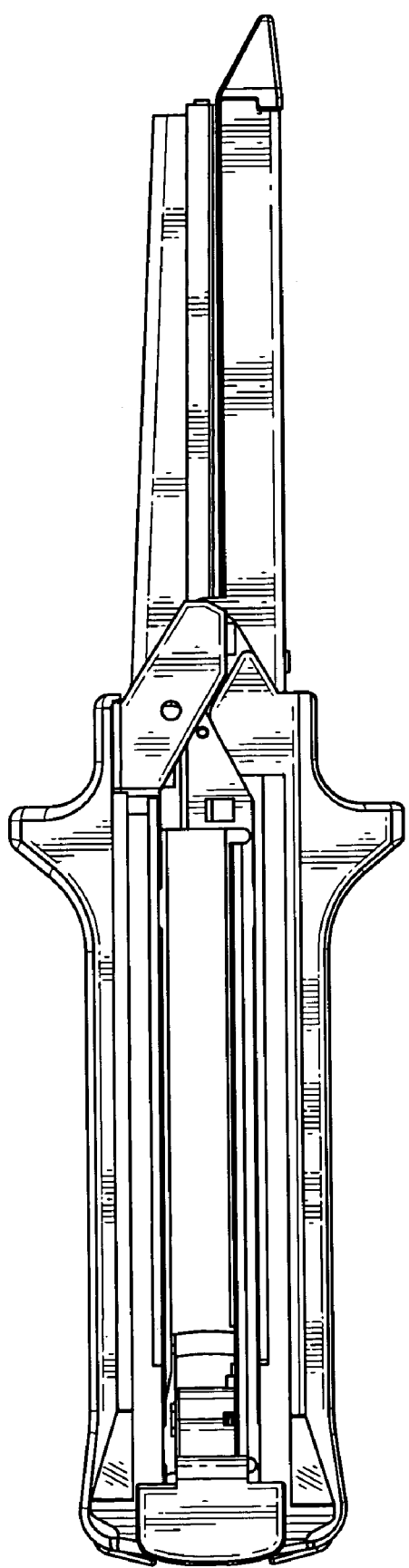
FIG. 4 is a side elevation view of the embodiment of FIG. 1 taken from the opposite side of that shown in FIG. 3.
Figure 5:
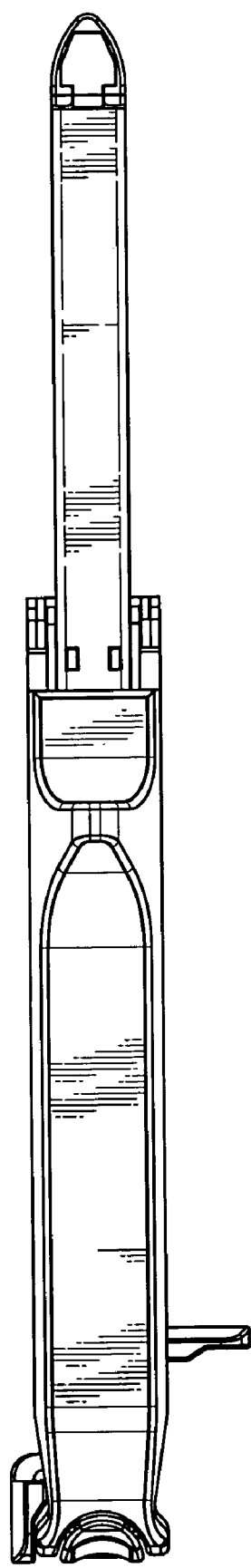
FIG. 5 is a bottom plan view of the embodiment of FIG. 1.
Figure 7:
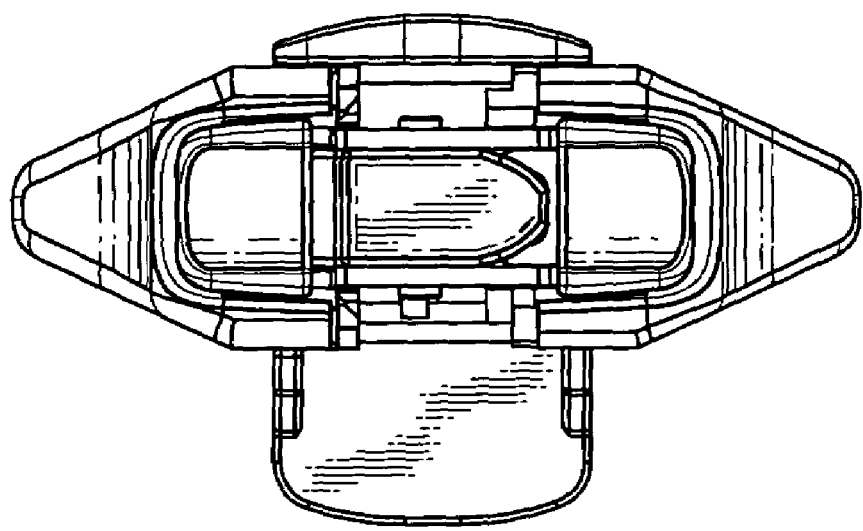
FIG. 7 is a rear elevation view of the embodiment of FIG. 1.
Figure 6:
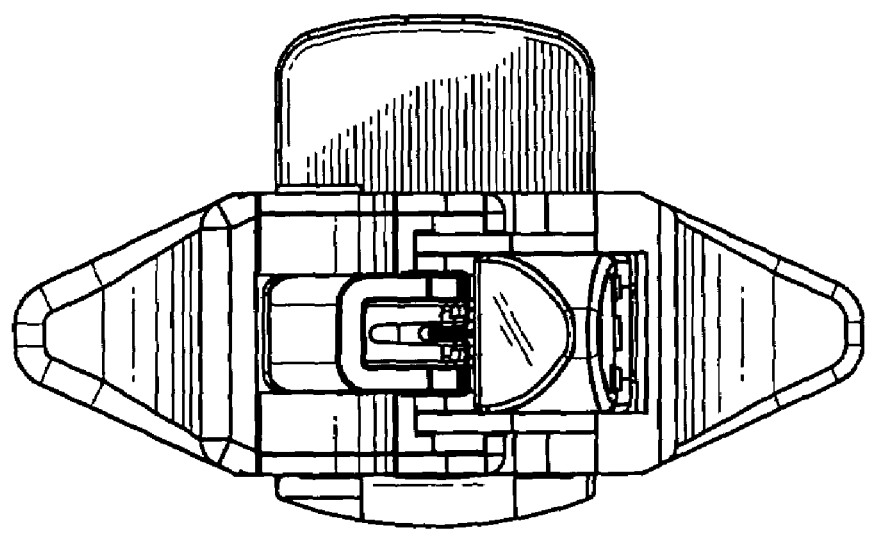
FIG. 6 is a front elevation view of the embodiment of FIG. 1.

Preferred embodiments of the presently disclosed surgical fastener apparatus will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring initially to FIG. 1, an illustrative embodiment of the presently disclosed surgical fastener apparatus is illustrated therein and designated generally as surgical stapler 10. Surgical stapler 10 is particularly adapted to apply a plurality of adjacent rows of staples to body tissue clamped in between the instrument's two principle sections, a cartridge receiving half-section 12 and an anvil half-section 14. Typical applications of the presently disclosed surgical fastener apparatus are, for example, creating a hemostatic seal in general, thoracic, and urologic surgery for resection, transection and creation of anastomoses. Specific tissue structures in which the instrument may be used are, for example, the stomach, the large and small bowels, lungs and the esophagus.

FIGS. 1–7 illustrate one preferred overall ornamental design for the presently disclosed surgical fastener applying apparatus wherein. Each of these various figures illustrates surgical stapler 10 with an anvil tip removed to illustrate the end cross-section profile of the anvil half-section. The anvil tip is the same as the tip on the distal end of the staple cartridge.

Figure 8:
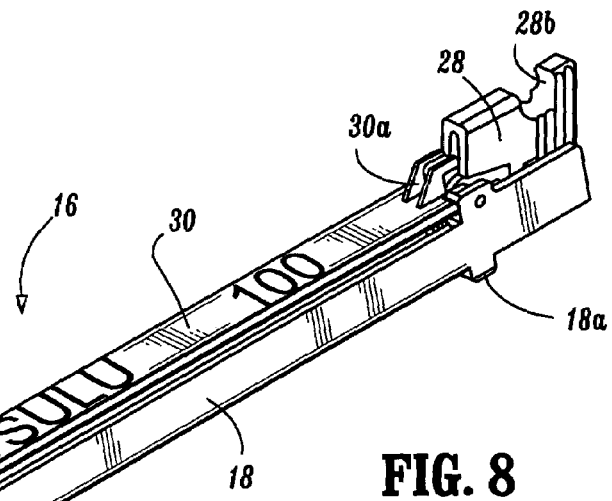
FIG. 8 is a perspective view of a disposable staple cartridge assembly of the presently disclosed surgical fastener applying apparatus.
Figure 9:
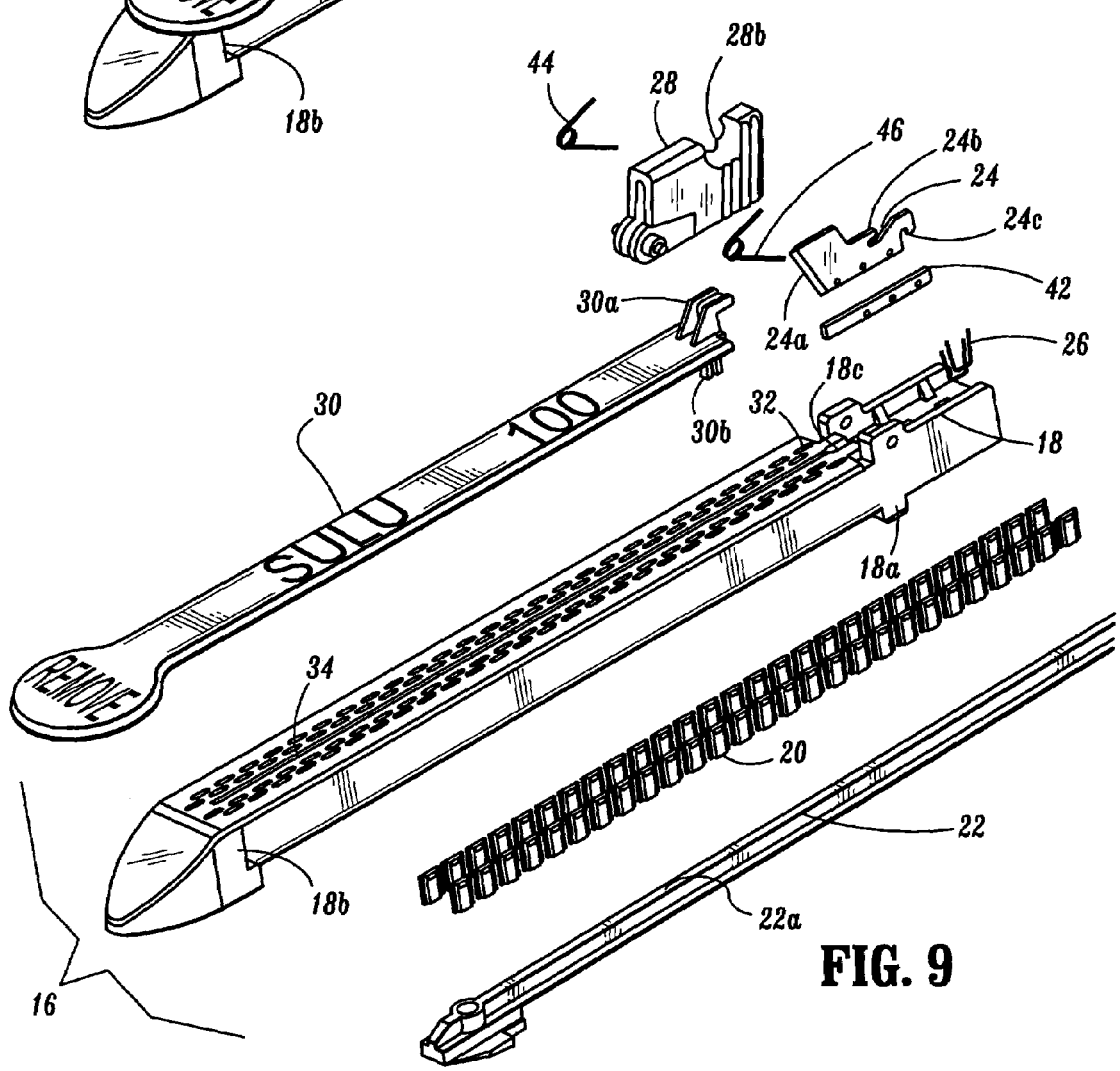
FIG. 9 is a perspective view with parts separated of the disposable staple cartridge assembly of FIG. 8.
Figure 10:
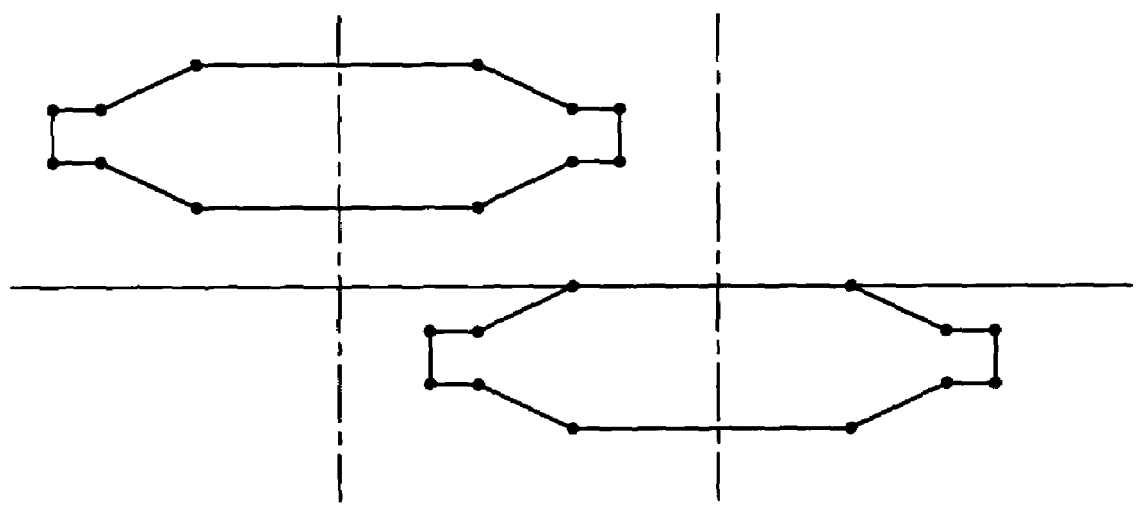
FIG. 10 is a schematic view of a staple pusher pair.

Referring to FIGS. 8–10, surgical stapler 10 is designed for use with a disposable staple cartridge assembly such as single use disposable loading unit ("SULU") 16 includes a cartridge body 18, a plurality of staple pusher members 20, a bottom cover 22, a knife 24 having an angled sharpened leading edge 24a, a plurality of staples 26, a pivotally mounted safety lockout 28 and a removable shipping wedge 30. As with known staple cartridge designs, cartridge body 18 has a plurality of rows of staple retaining slots 32 formed therein. Surgical stapler 10 may be manufactured and assembled in different sizes to receive different size SULUs 16. For example, surgical stapler 10 can be made in different sizes to accept SULUs having staple line lengths of 60 mm, 80 mm, and 100 mm.

Alternatively, SULUs 16 may be adapted such that one common surgical stapler 10 will accept multiple different staple count SULUs. For example, SULUs 16 may be configured such that each different staple count SULU shares a common size cartridge body 18 to facilitate mounting on surgical stapler 10.

In the illustrated embodiment, there are two staggered rows of slots 32 formed on either side of a linear slotted track 34 which guides knife 24 during its longitudinal movement. A single staple 26 is positioned in each of slots 32. The staple rows preferably extend a distance distally beyond the distal end of knife track 34 to facilitate staple formation beyond the stroke length of knife 24.

Staple pushers 20 are aligned one each with slots 32 such that a single staple pusher 20 is positioned under the staple 26 retained in slot 32. Staple pushers 20 are formed such that they are attached to each other in groups of two offset oriented pusher pairs, shown schematically in FIG. 10, and have an actuating surface connecting each pair of two pushers 20.

Figure 11:
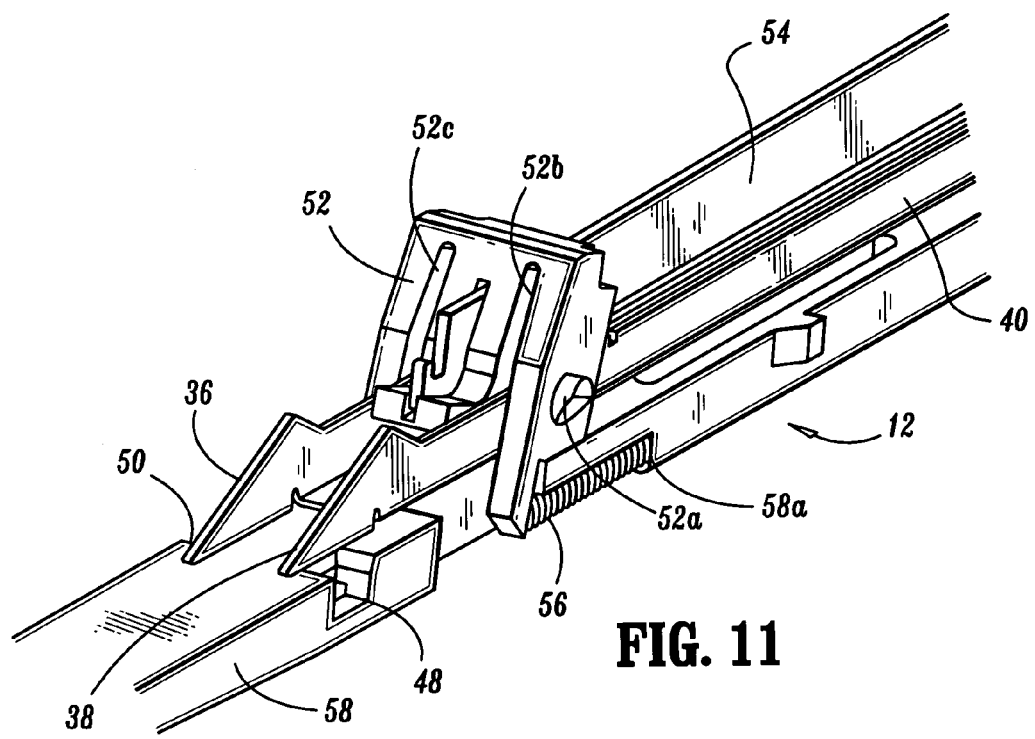
FIG. 11 is an enlarged left distal perspective view of a staple cartridge loading and lockout mechanism.

The pusher pairs are arranged in two series, one on each side of slotted track 34, such that the actuating surfaces of each series of pusher pairs forms a line centered between the staggered row of staples 26. The actuating surfaces act as cam followers and interact with a pair of staggered camming surfaces 36, 38 (see FIG. 11) extending from a cam bar channel 40 to expel the pairs of staples 26 on each side of the knife track 34. As illustrated, camming surfaces 36, 38 form a single angle relative to horizontal. In certain application, for example, with staples having an unformed leg height of about 4.5 mm, camming surfaces 36, 38 may be formed of a plurality of angles to facilitate optimal staple deformation with a given firing force. As cam bar channel 40 is moved distally this sequence is repeated until the distal movement of cam bar channel 40 is either stopped intentionally by the user to form less than all of staples 26 or until all of staples 26 are expelled from SULU 16.

Bottom cover 22 partially encloses the bottom of a channel formed by the upper surface and side walls of cartridge body 18. A longitudinal ridge 22a is formed on the upper surface of bottom cover 22 and serves as a bearing surface for knife bearing channel 42 secured to the bottom edge of knife 24 as it travels in knife track 34. A pair of slots are formed one on either side of longitudinal ridge 22a. The outer limit of each slot being defined by the outer wall of cartridge body 18 on the respective side of ridge 22a. These slots facilitate reciprocating longitudinal movement of the camming surface extensions 36, 38 of cam bar channel 40. Knife bearing channel 42 which is wider than knife track 34, is secured to the bottom surface of the knife such that knife bearing channel member 42 rides between knife track 34 and longitudinal ridge 22a of bottom cover 22. In this manner, knife 24 is prevented from undergoing substantial vertical movement during longitudinal translation in knife track 34.

Safety lockout 28 is pivotably disposed on the upper proximal end of cartridge body 18 and is movable from a locked orientation to an unlocked orientation. Preferably, safety lockout 28 is biased away from the locked orientation towards an orientation substantially perpendicular to the longitudinal axis of cartridge body 18. Any suitable bias member may be utilized such as, for example, springs 44, 46. To overcome the bias towards the perpendicular orientation, safety lockout 28 includes a transverse horizontal surface 28a (see FIG. 24) formed on the underside thereof which engages a hook 24b formed on the upper edge surface of knife 24. This cooperative engagement serves to retain safety lockout 28 in the locked orientation wherein safety lockout 28 covers knife 24.

When surgical stapler 10 has been unclamped, as will be described in greater detail further herein, after either partial or complete firing, safety lockout 28 is biased to the perpendicular orientation (see FIGS. 17 and 18), extending upwardly away from cartridge half-section 12. In this manner, surgical stapler 10 cannot be re-clamped until the partial or completely fired SULU 16 is removed and replaced with a new SULU 16. Safety lockout 28 also provides a cut-out grasping surface 28b with which SULU 16 may readily be removed from surgical stapler 10.

As previously noted, shipping wedge 30 is removably attachable to cartridge body 18. When installed on SULU 16, shipping wedge 30 covers the entire surface area of the staple rows 26 and knife track 34. Additionally, shipping wedge 30 includes an abutment 30a extending upwardly and proximally from the upper proximal surface of shipping wedge 30. Abutment 30a in cooperation with safety lockout 28 covers sharpened distal edge 24a of knife 24. This feature prevents the knife from being exposed to the user during handling of SULU 16. Additionally, abutment 30a prevents pivotal movement of safety lockout 28 from the locked orientation. Thus, even if SULU 16 is properly loaded on surgical stapler 10, staples 26 cannot be fired until shipping wedge 30 is first removed.

Shipping wedge 30 also includes a post 30b extending downwardly from the underside near the proximal end. Post 30b fits into a complementary shaped opening 18c formed in cartridge body 18 at the proximal end of knife track 34. With shipping wedge 30 in place, post 30b blocks potential distal movement of knife 26. In an alternative embodiment, SULUs 16 may also be provided without a knife in applications where it is desirable to perform stapling without transection. In such an embodiment, knife 26 is replaced with a blank element to substitute for the knife to interact with safety lockout 28.

Figure 13:
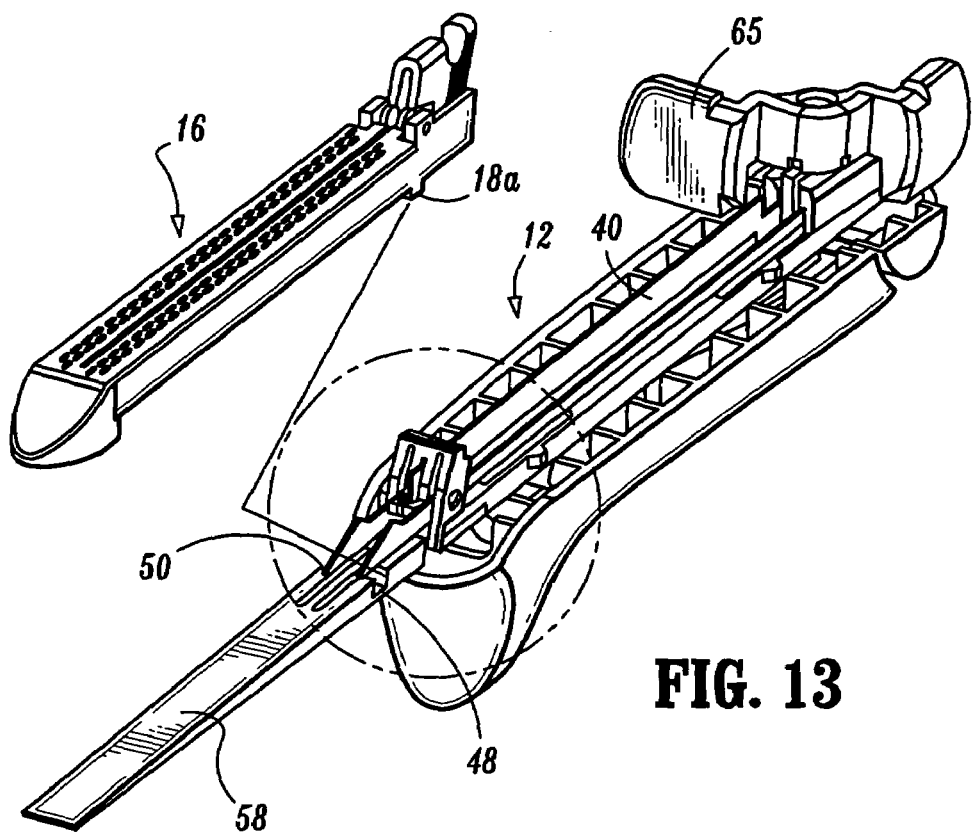
FIG. 13 is a perspective view with parts separated showing installation of a staple cartridge assembly on a cartridge half-section of the presently disclosed surgical fastener applying apparatus.

Cartridge body 18 is provided with several molded surfaces to facilitate mounting and alignment of SULU 16 with respect to cartridge half-section 12 of surgical stapler 10. Such alignment facilitating surfaces may be formed at any suitable location on the various components of cartridge body 18 to correspond with complementary surfaces on cartridge half-section 12. In the illustrated embodiment, locating/alignment feature surfaces 18a are formed extending downwardly on either side of SULU 16 near the proximal end thereof and molded surfaces 18b are formed on either side of cartridge body 18 near the distal end thereof. When SULU 16 is properly installed on surgical stapler 10, surfaces 18a seat in a pair of notches 48, 50 (see FIG. 13) formed in cartridge half-section 12.

Referring to FIGS. 11–16, a loading and lockout mechanism for SULU 16 will now be described in detail. In these figures, a channel frame 12a (see FIG. 21) of cartridge half-section 12 is not shown so that the loading and lockout mechanism can be illustrated more clearly. The loading and lockout mechanism facilitates loading of SULU 16 and prevents firing of surgical stapler 10 until SULU 16 is properly loaded on cartridge half-section 12 and surgical stapler 10 is properly clamped shut. The loading and lockout mechanism includes a rocker 52 which is pivotably mounted to channel frame 12a (see FIG. 21) of cartridge half-section 12 by way of transversely extending post portions 52a seating in openings formed through the sidewalls of channel frame 12a. Post portions 52a are provided with angled downwardly oriented surfaces to facilitate assembly of rocker 52 with channel frame 12a. Rocker 52 is preferably a molded plastic component and is provided with three slots, namely an open bottomed slots 52b, 52c to permit longitudinal movement of cam bar channel 40 and a closed slot 52d to permit passage of a center bar 54.

Figure 12:
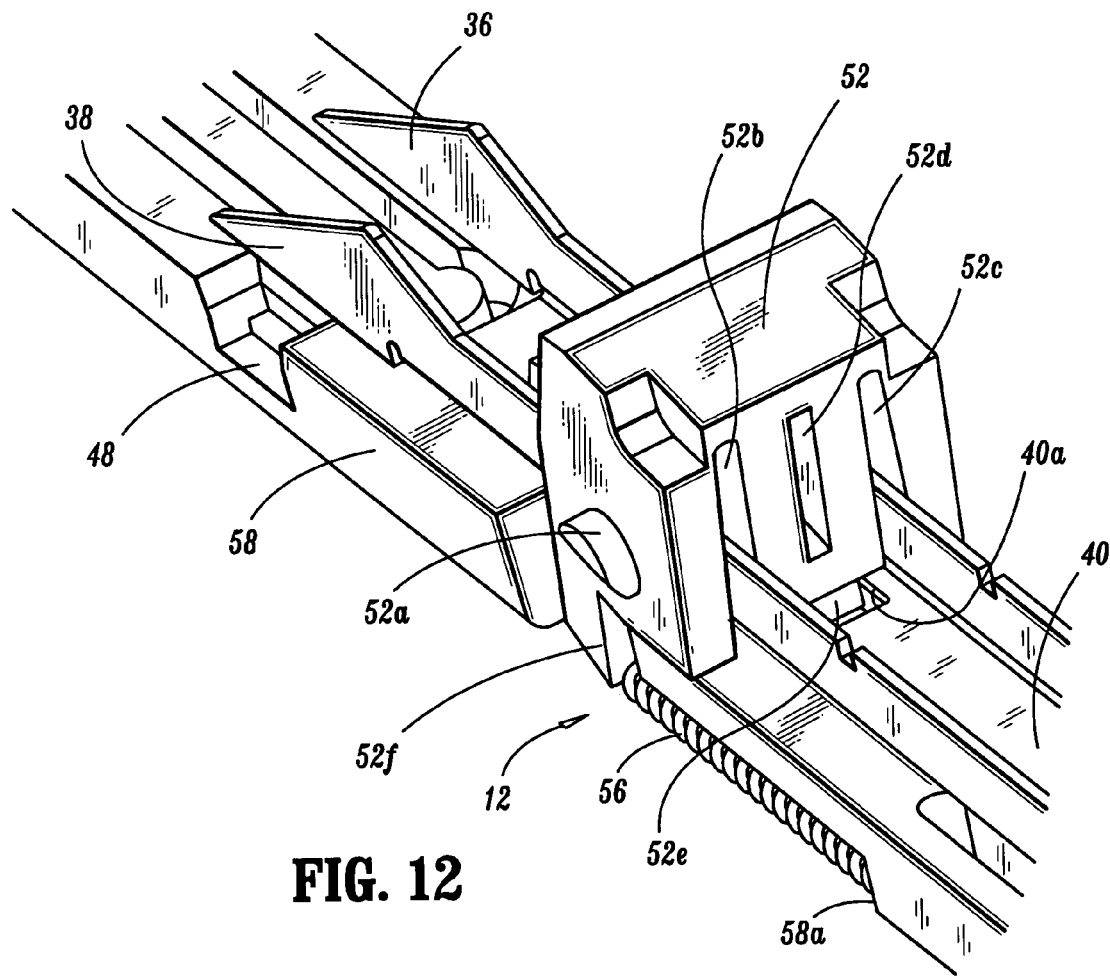
FIG. 12 is an enlarged right side proximal perspective view of the loading and lockout mechanism of FIG. 11.
Figure 14:
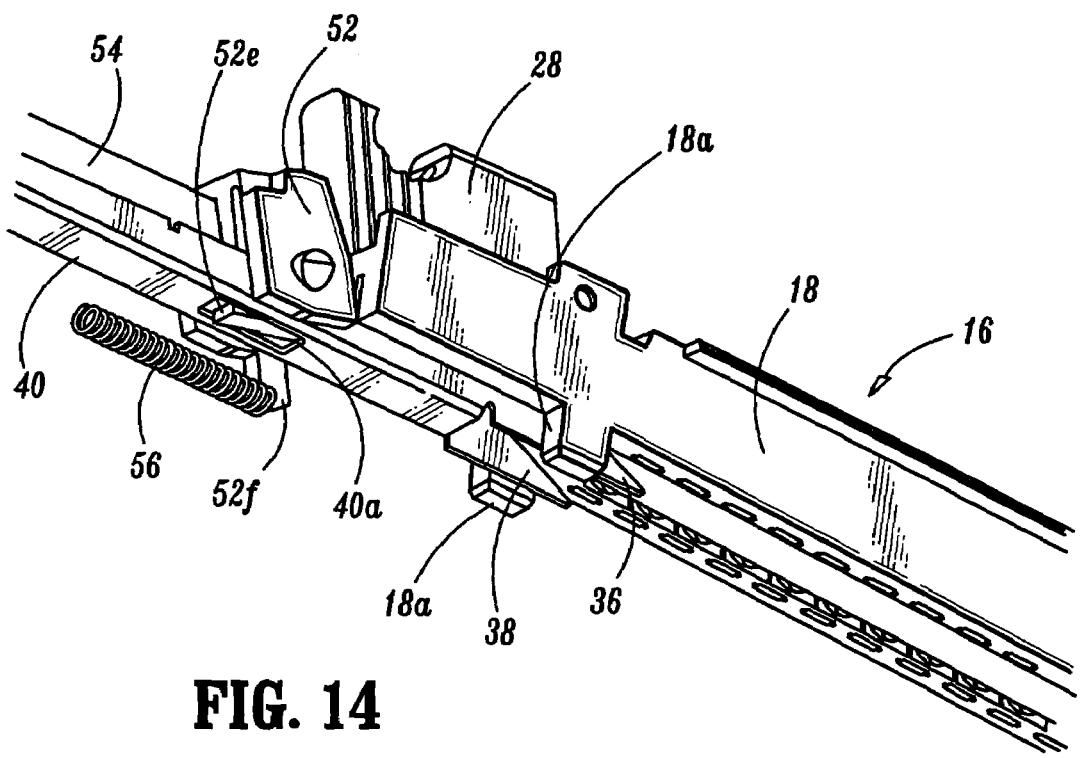
FIG. 14 is an enlarged perspective view from the bottom of the loading and lockout mechanism with a staple cartridge in place thereon.

As best shown in FIGS. 12 and 14, rocker 52 is further provided with a downwardly extending blocking surface 52e which is in vertical alignment with an opening formed through the bottom surface of cam bar channel 40 when cam bar channel 40 is in its proximal-most position. Rocker 52 is biased, by way of a spring 56 being disposed between downwardly extending leg 52f and an end wall 58a of a beam member 58, toward a locked-out position wherein blocking surface 52e extends through opening 40a. In this manner, cam bar channel 40 is prevented from distal longitudinal movement. In versions of surgical stapler 10 using shorter SULUs 16, beam 58 may be eliminated.

Figure 15:
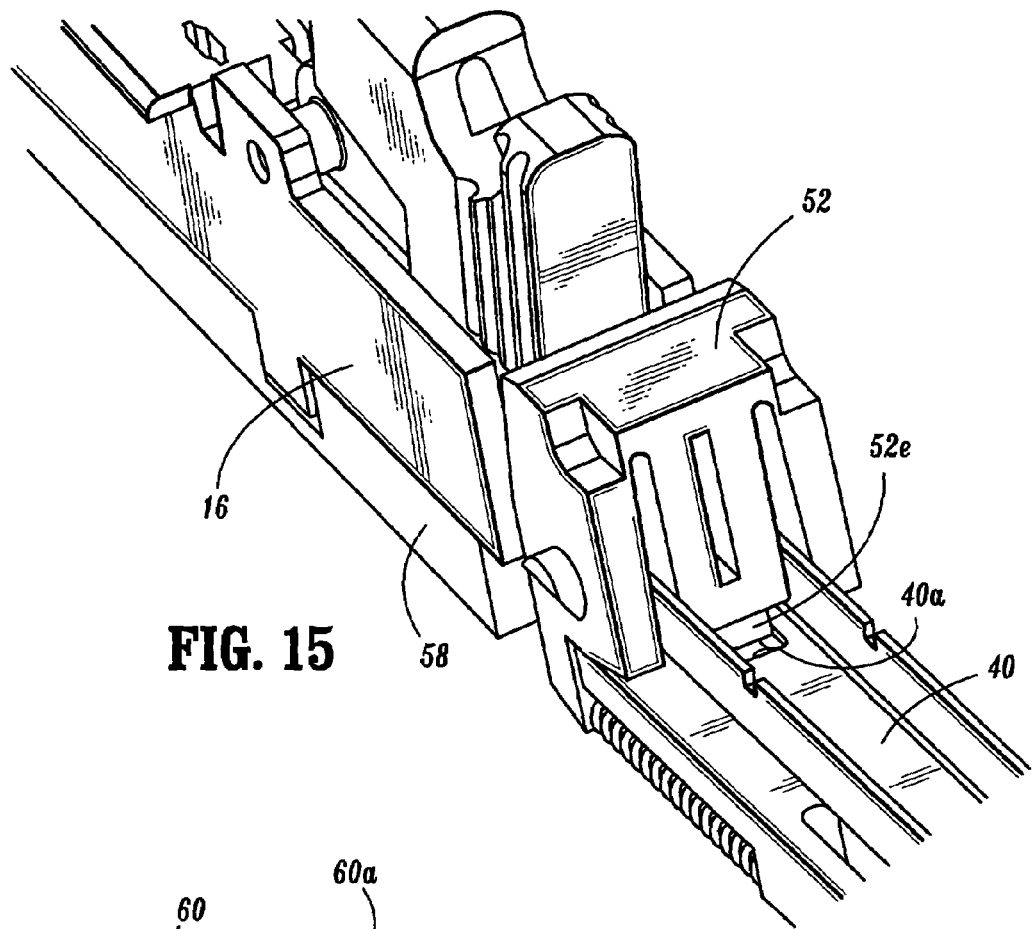
FIG. 15 is an enlarged perspective view similar to FIG. 12, with a staple cartridge in place.
Figure 16:
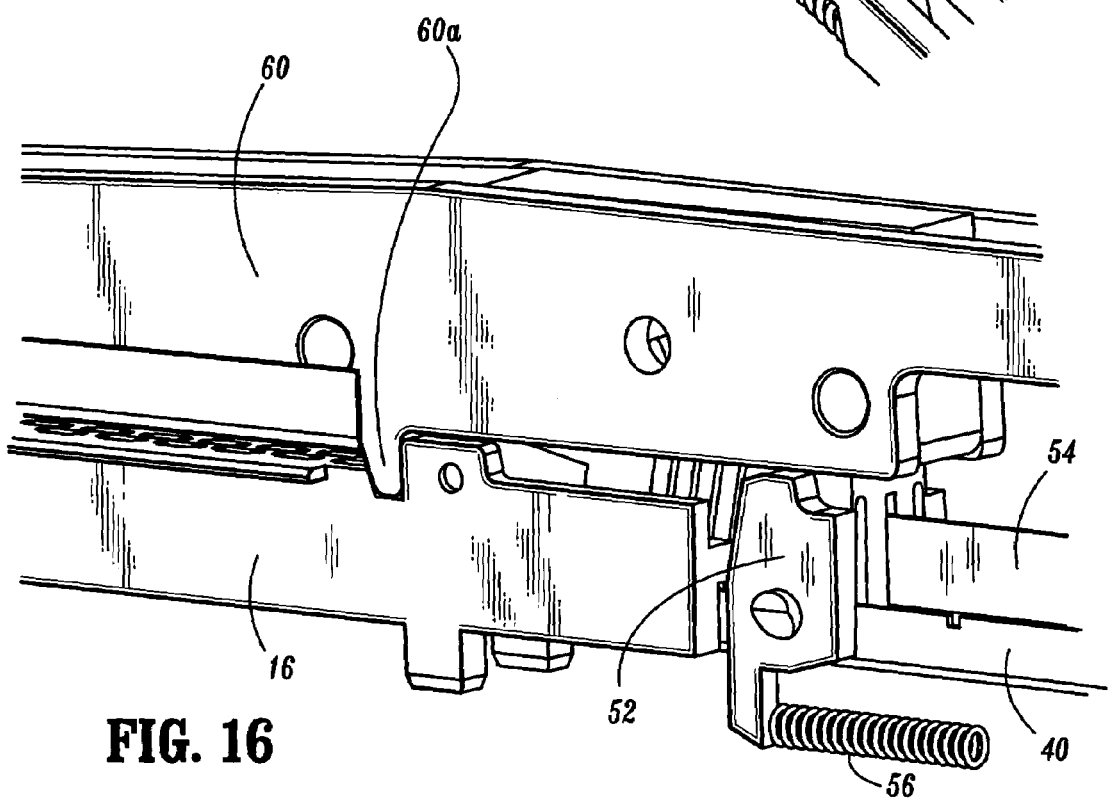
FIG. 16 is an enlarged side perspective view which shows the relative positioning of the loading and lockout mechanism with a staple cartridge installed and with an anvil half-section in place in a clamped condition.

Upon loading of SULU 16 on cartridge half-section as shown in FIGS. 15 and 16, the spring bias maintains rocker 52 in the locked-out position. It is only when anvil half-section 14 is joined with cartridge half-section 12 and the half-sections clamped together thereby causing downwardly extending leg portions 60a formed on either side of anvil half-section channel member 60 to bias against SULU 16, that rocker 52 is urged to rotate by the camming action of proximal end surface of SULU 16 against the distal end surface of rocker 52. In this manner, blocking surface 52e is moved out of longitudinal alignment with opening 40a of cam bar channel 40 thereby permitting distal longitudinal movement thereof.

Figure 18:
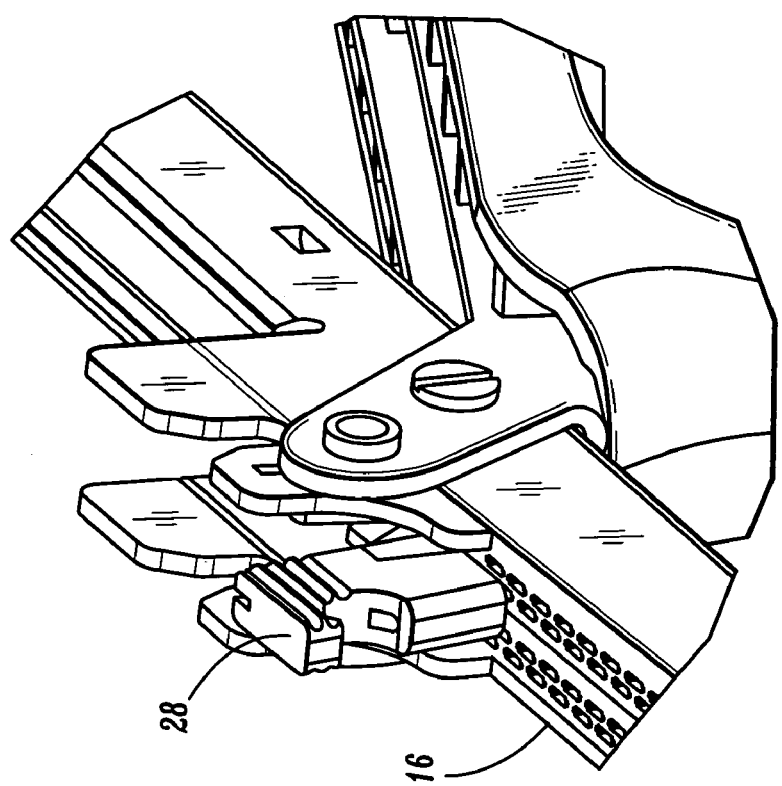
FIG. 18 is an enlarged view of the indicated area of detail of FIG. 17.
Figure 17:
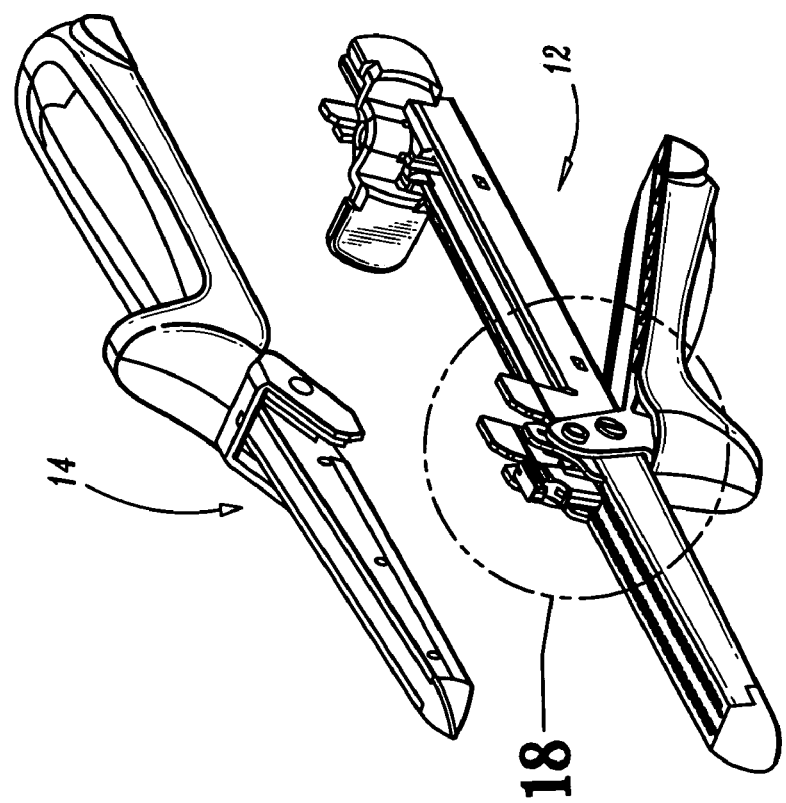
FIG. 17 is a perspective view which shows a surgical stapler apparatus after partial or complete firing in an unclamped condition with a staple cartridge safety lockout in a locked out position.

Referring to FIGS. 17 and 18, once surgical stapler 10 has been at least partially fired, if the instrument is opened, safety lockout 28 of SULU 16 automatically moves to the perpendicular orientation due to the spring bias mounting thereof. In this orientation, surgical stapler 10 cannot be re-clamped. Thus, if the user desires to apply further staples, SULU 16 must first be removed and replaced with a non-fired SULU 16.

Figure 19:
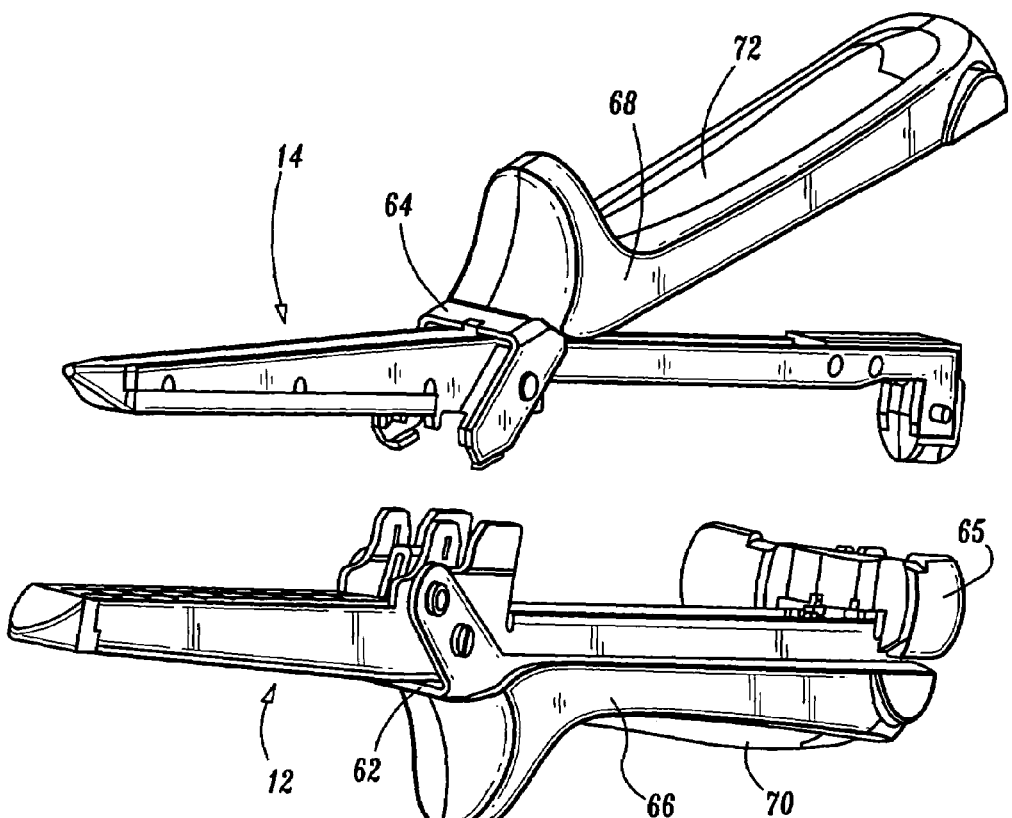
FIG. 19 is a perspective view of the surgical stapler apparatus opened from an anvil half-section side with an anvil half-section clamp lever opened and a cartridge half-section clamp lever closed.
Figure 20:
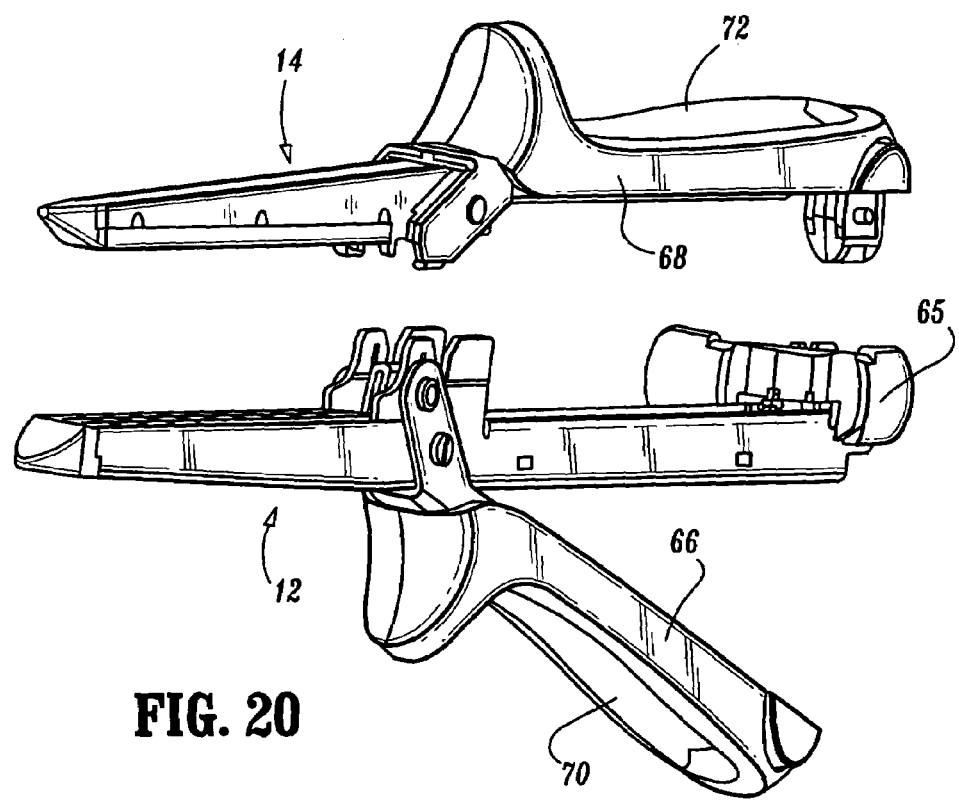
FIG. 20 is a perspective view of the surgical stapler apparatus opened from a cartridge half-section side with a cartridge half-section clamp lever opened and an anvil half-section clamp lever closed.
Figure 21:
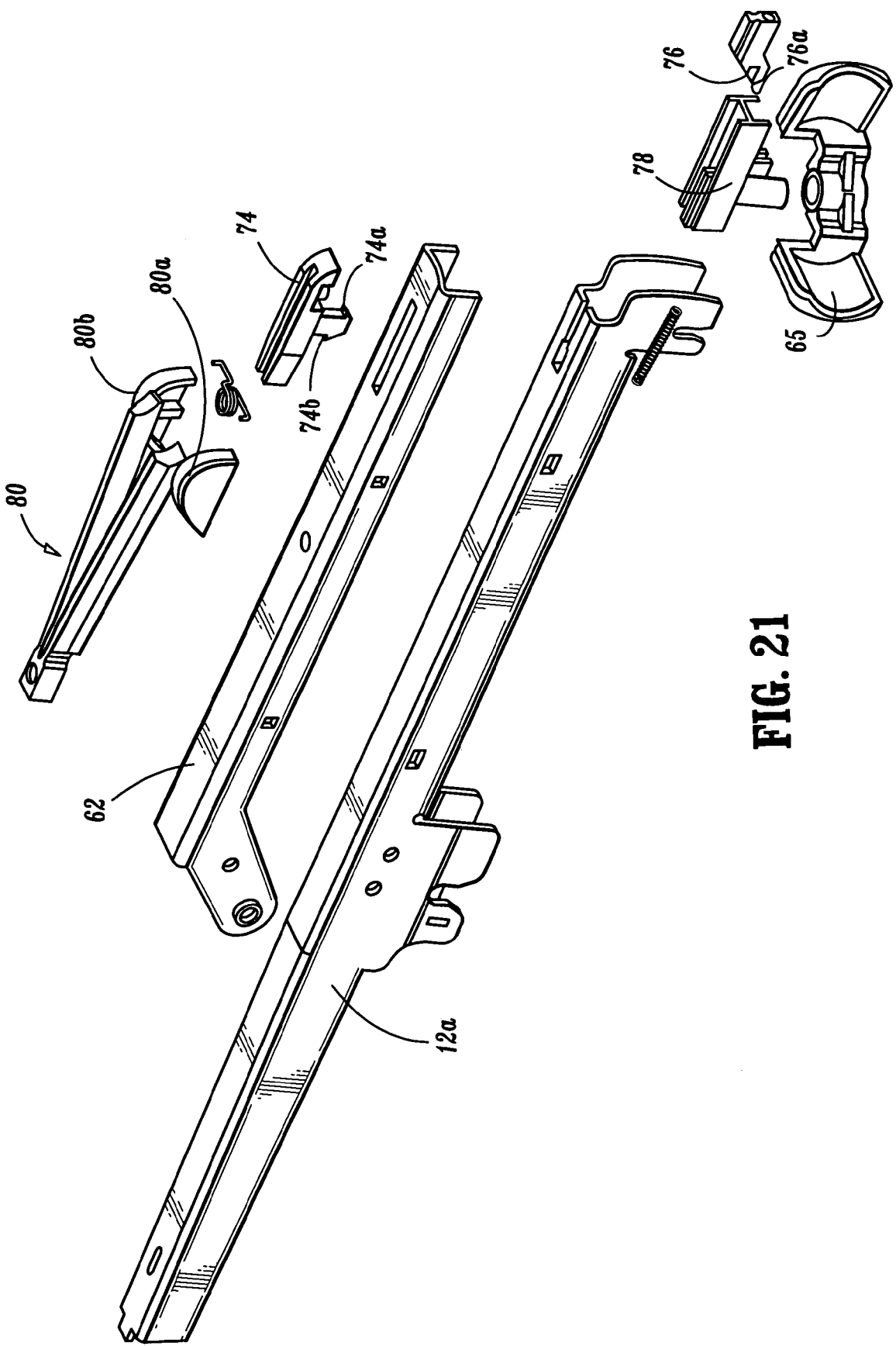
FIG. 21 is a perspective view with parts separated which shows the structural relationship of the various components of a clamp lever lockout and safety interlock mechanism.

Referring to FIGS. 19–21, surgical stapler 10 is provided with dual selectable clamping levers 62, 64 and a pivotably mounted firing lever 65. Clamping levers 62, 64 provide the user with the uniquely novel option of opening surgical stapler 10 from either half-section 12 or 14. Additionally, firing lever 65 provides the user with the ability to fire surgical stapler 10 from either the left or right side.

Clamping levers 62, 64 are pivotably mounted to cartridge half-section 12 and anvil half-section 14, respectively. A pair of ergonomic contoured handles 66, 68 are secured to clamping levers 62, 64, respectively to provide the user with a convenient gripping handle. To further enhance the gripping of surgical stapler 10 by the user, a pair of friction enhancing inserts 70, 72 are secured to handles 66, 68. Inserts 70, 72 may be formed of any suitable friction enhancing materials, for example, rubber. Half-sections 12 and 14 are preferably configured and dimensioned to provide the ability for the user to reach around both halves and comfortably close surgical stapler 10 with a one-handed operation to approximate the captured tissue.

Referring to FIGS. 21–23, 25–27 and 29, a clamp latch and safety interlock mechanism is provided at the proximal end of surgical stapler 10. The clamp latch and safety interlock mechanism serves to retain clamp levers 62, 64 in a clamped orientation as well as to provide a safety interlock which prevents openings of either clamp lever 62, 64 once firing lever 65 is moved distally. Each half section 12 and 14 is provided with a clamp latch and safety interlock assembly which is essentially the same and which work to latch clamp levers 62, 64 in a clamped configuration upon squeezing the clamp levers 62, 64 to the closed position. Accordingly, the following description of the various components which make up the assembly will be directed to that for the cartridge half-section 12 as shown in FIG. 21.

The clamp latch and safety interlock mechanism includes a distal clamp lever latch 74 and a proximal interlock latch 76 which is spring biased distally toward a latched position. When surgical stapler 10 is in the clamped configuration with firing lever 65 in the proximal-most position, a firing slide block 78 biases latch 76 proximally to overcome the distal spring bias, as shown in FIG. 25, to position ledge 76a of latch 76 out of lateral alignment with proximal ledge 74a formed on latch 74 thereby positioning latch 76 in an unlatched position. In this position, the user either clamp lever 62, 64 by squeezing spring biased finger pad portions 80a, 80b of latch handle release member 80 which urges latch 74 proximally such that distal ledge 74b is moved out of lateral alignment with the blocking structure formed on cartridge half-section 12a or anvil half-section 14a (not shown).

Once firing lever 65 is moved distally to begin the firing sequence of surgical stapler 10, as shown in FIGS. 26, 27 and 29, slide block 78 also moves distally thereby removing the biasing force which overcame the distal spring bias of latch 76. Thus, ledge 76a moves in to lateral alignment with ledge 74a of latch 74 thereby preventing clamp lever 62 from being opened until firing lever 65 is once again moved to the proximal-most position. The instrument is thereby prevented from opening during the firing stroke.

Figure 30:
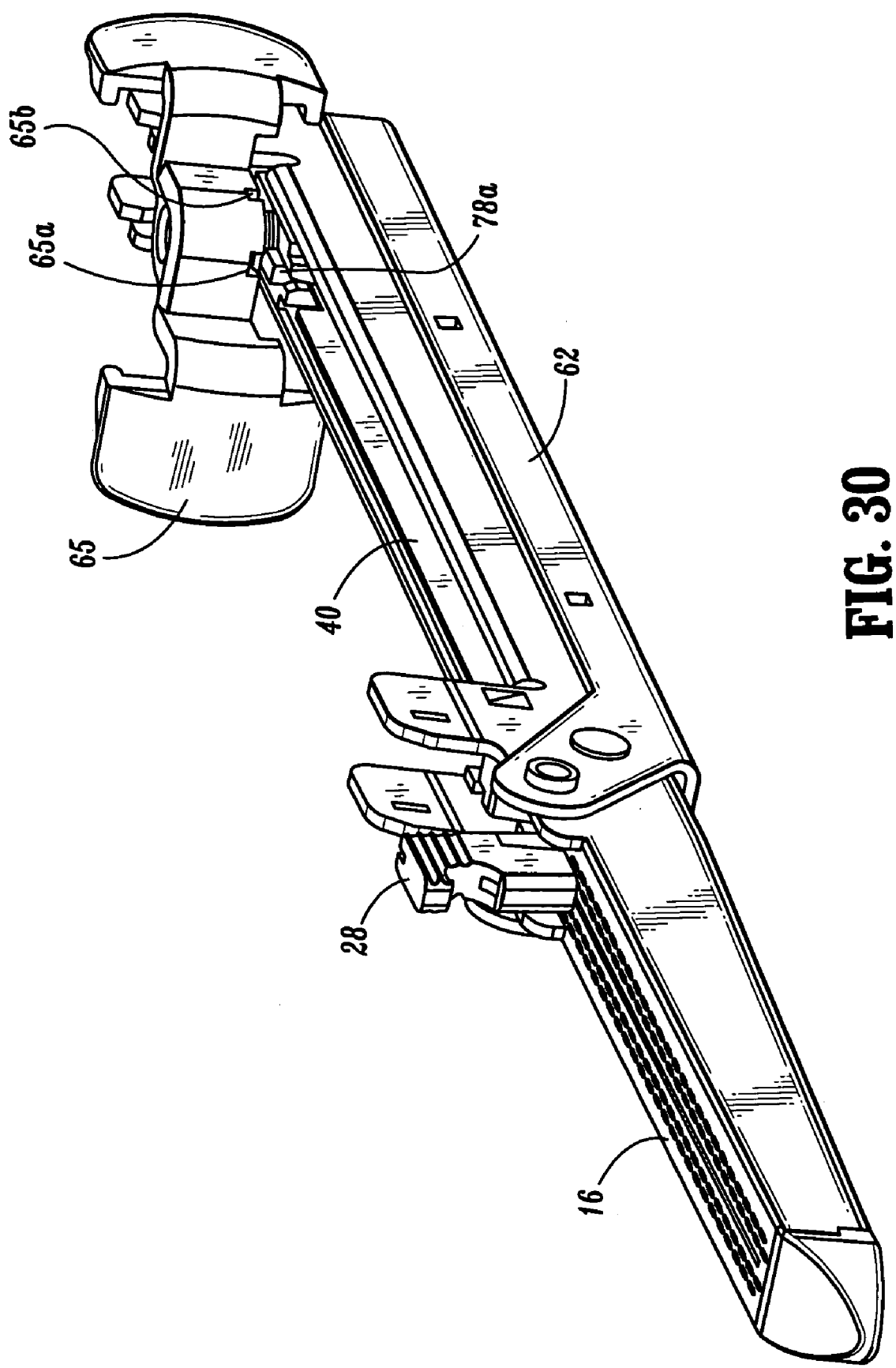
FIG. 30 is a perspective view of the cartridge half-section of the surgical stapler apparatus.
Figure 31:
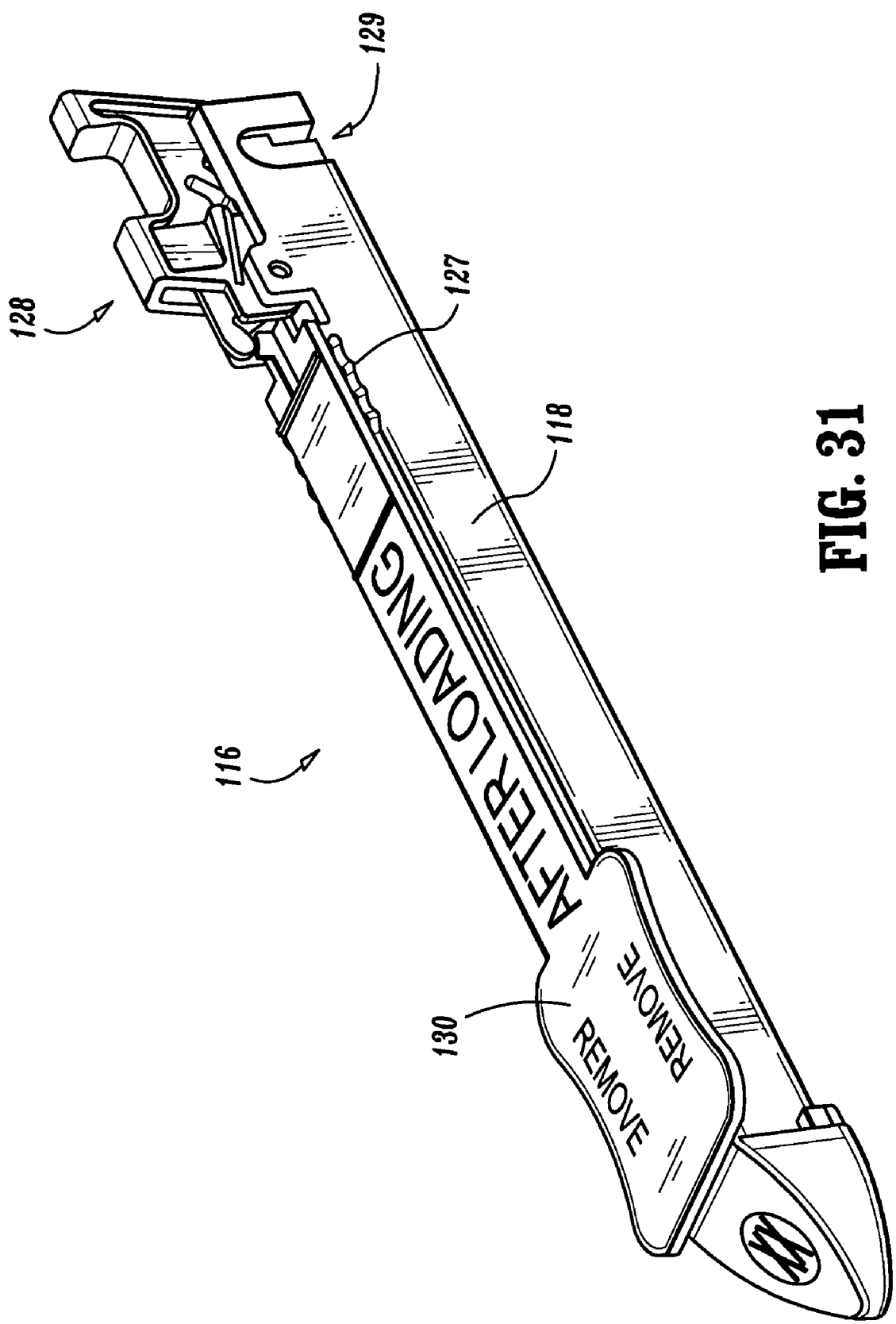
FIG. 31 is a perspective view of a disposable staple cartridge assembly according to an alternative embodiment of the present invention.
Figure 32:
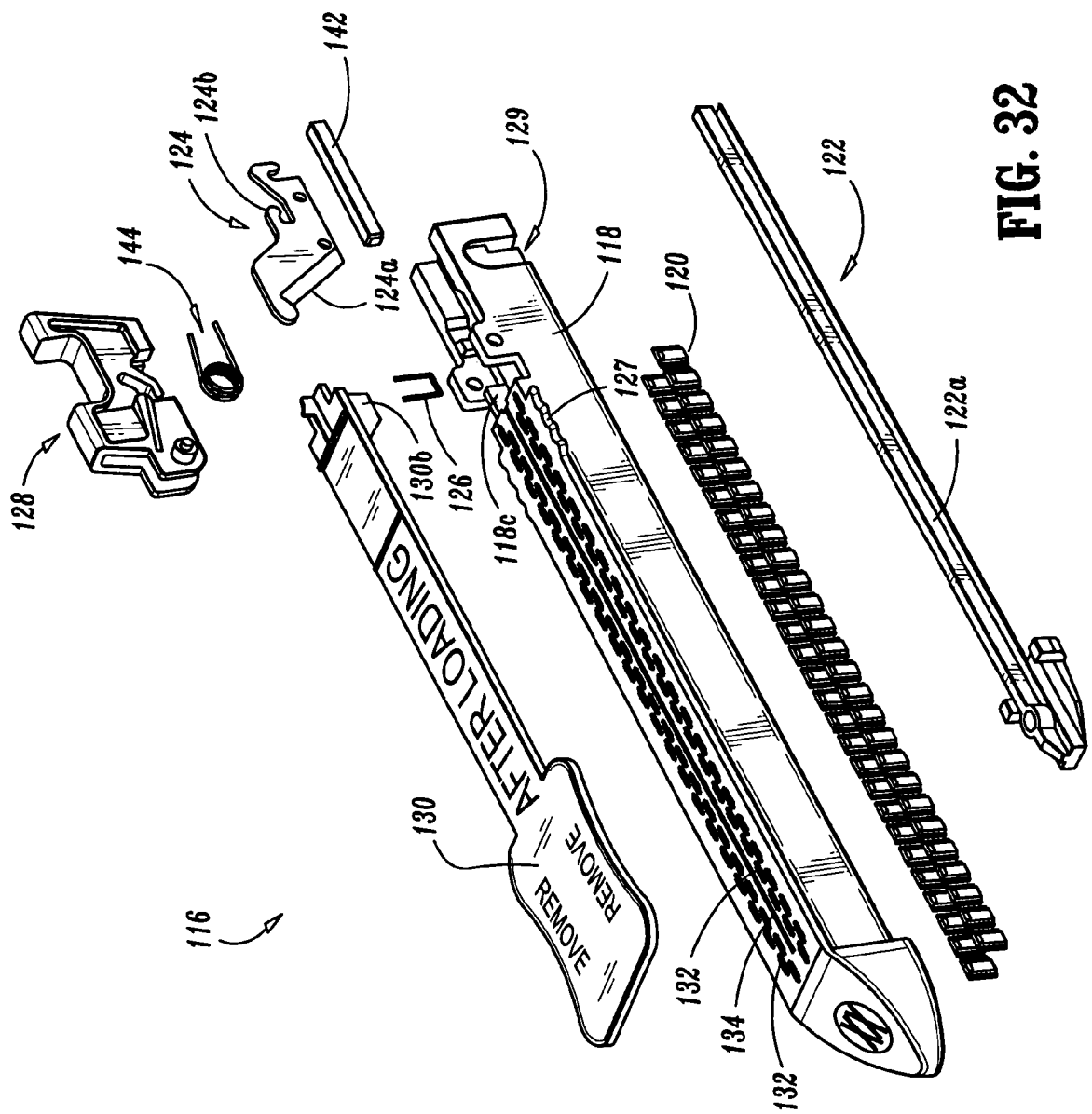
FIG. 32 is a perspective view, with parts separated, of the disposable staple cartridge assembly of FIG. 31.
Figure 33:
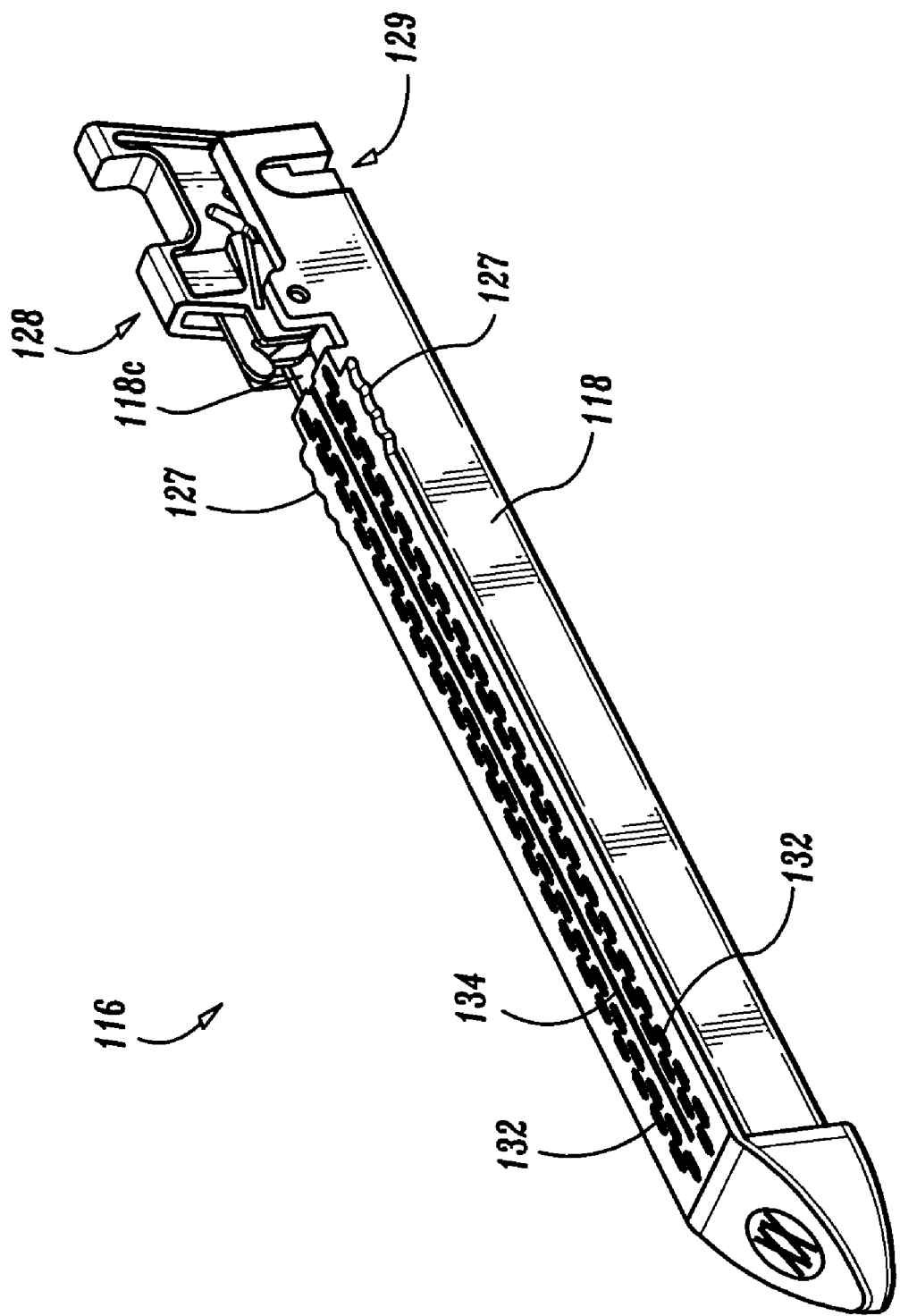
FIG. 33 is a perspective view of the disposable staple cartridge assembly as shown in FIG. 31 with the shipping wedge removed therefrom.
Figure 34:
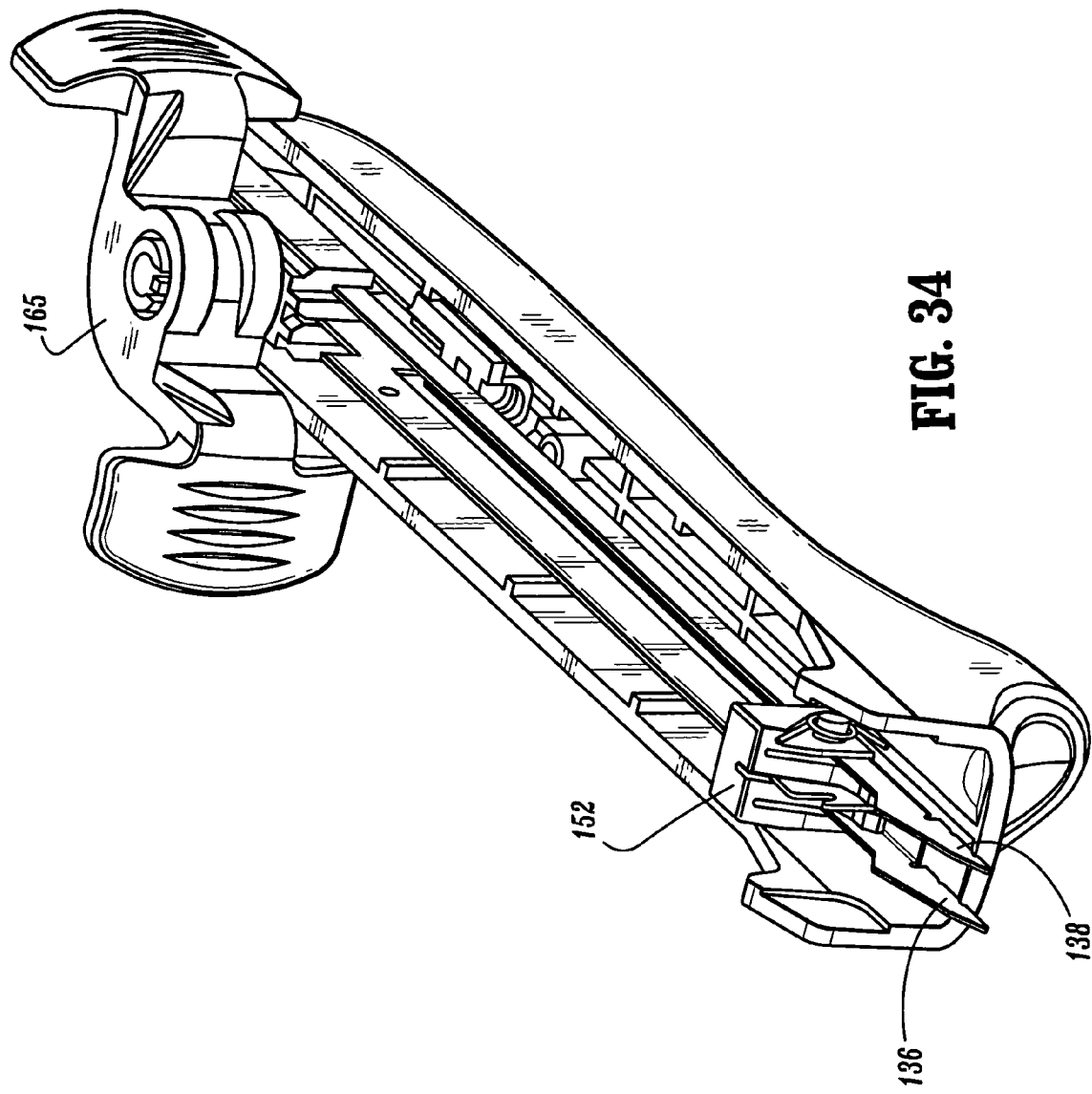
FIG. 34 is a perspective view of a cartridge half-section according to the alternative embodiment of the present invention.
Figure 36:
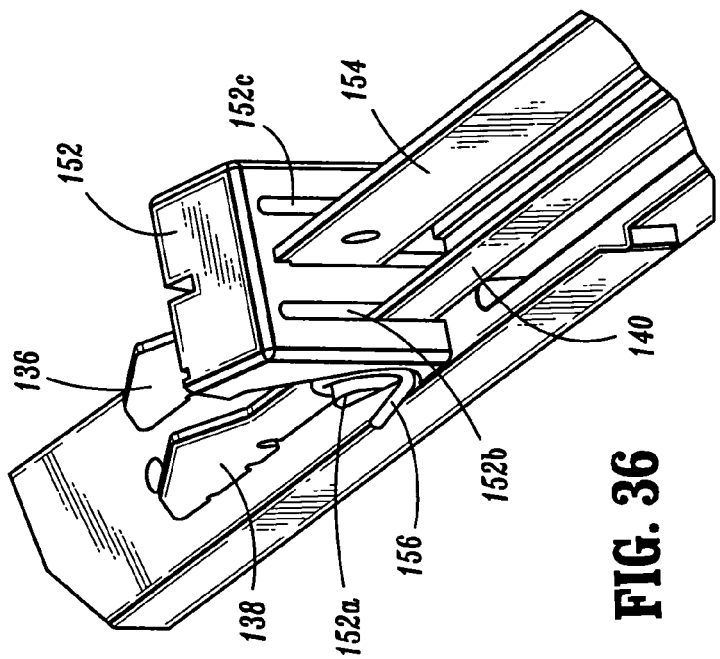
FIG. 36 is an enlarged right side proximal perspective view of the loading and lockout mechanism of FIG. 35.
Figure 35:
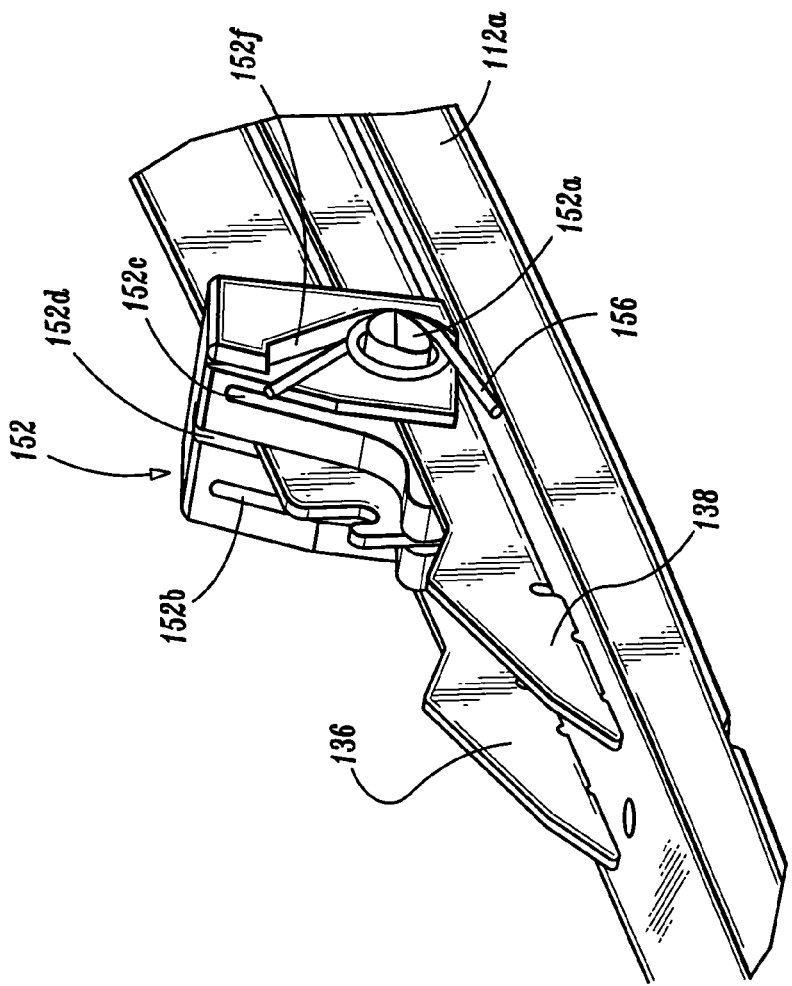
FIG. 35 is an enlarged left distal perspective view of a staple cartridge loading and lockout mechanism.

Upon initial distal movement, firing lever 65 becomes locked-out from pivotal movement by way of firing lever 65 being cammed downwardly to overcome an upward spring bias, as shown in the operationally progressive views of FIGS. 25 and 29. In particular, as best shown in FIG. 30, recessed notches 65a, 65b are formed as keyways which engage a key 78a formed on slide block 78, respectively depending upon which side firing lever 65 is rotated to during firing. Firing lever 65 can be returned to the proximal-most position at any time during the firing stroke. Firing lever 65 must be returned to the proximal-most position before the levers can be released and the instrument unclamped. As described previously, if the instrument is opened after firing either partially or completely, safety lockout 28 on SULU 16 is configured to prevent the user from re-clamping the instrument.

Turning now to FIGS. 31–51, an alternative embodiment of a disposable staple cartridge assembly is generally shown as 116. Staple cartridge assembly 116 includes a cartridge body 118, a plurality of staple pusher members 120, a bottom cover 122, a knife 124 having an angled sharpened leading edge 124*a*, a plurality of staples 126, a pivotally mounted safety lockout 128 and a removable shipping wedge 130. As with known staple cartridge designs, cartridge body 118 has a plurality of rows of staple retaining slots 132 formed therein.

Alternatively, cartridge assembly 116 may be adapted such that one common surgical stapler 100 (see FIGS. 41 and 42) will accept multiple different staple count cartridge assemblies 116. For example, cartridge assembly 116 may be configured such that each different staple count cartridge assembly 116 shares a common size cartridge body 118 to facilitate mounting on surgical stapler 100.

In the present illustrated embodiment, there are two staggered rows of slots 132 formed on either side of a linear slotted track 134 which guides knife 124 during its longitudinal movement. A single staple 126 is positioned in each of slots 132. The staple rows preferably extend a distance distally beyond the distal end of knife track 134 to facilitate staple formation beyond the stroke length of knife 124. Staple pushers 120 are formed such that they are attached to each other in groups of two offset oriented pusher pairs.

The pusher pairs are arranged in two series, one on each side of slotted track 134, such that the actuating surfaces of each series of pusher pairs forms a line centered between the staggered row of staples 126. The actuating surfaces act as cam followers and interact with a pair of staggered camming surfaces 136 and 138 (see FIGS. 34–36) extending from a pair of cam bars 140 to expel the pairs of staples 126 on each side of the knife track 134. As illustrated, camming surfaces 136 and 138 form a single angle relative to horizontal. As each cam bar 140 is moved distally this sequence is repeated until the distal movement of each cam bar 140 is either stopped intentionally by the user to form less than all of staples 126 or until all of staples 126 are expelled from cartridge assembly 116.

Bottom cover 122 partially encloses the bottom of a channel formed by the upper surface and side walls of cartridge body 118. A longitudinal ridge 122*a* is formed on the upper surface of bottom cover 122 and serves as a bearing surface for knife bearing channel 142, secured to the bottom edge of knife 124, as knife 124 travels in knife track 134. A pair of slots are formed one on either side of longitudinal ridge 122*a*. The outer limit of each slot being defined by the outer wall of cartridge body 118 on the respective side of ridge 122*a*. These slots facilitate reciprocating longitudinal movement of the camming surface extensions 136, 138 of each cam bar 140. Knife bearing channel 142 which is wider than knife track 134, is secured to the bottom surface of the knife such that knife bearing channel member 142 rides between knife track 134 and longitudinal ridge 122*a* of bottom cover 122. In this manner, knife 124 is prevented from undergoing substantial vertical movement during longitudinal translation in knife track 134.

Safety lockout 128 is pivotably disposed on the upper proximal end of cartridge body 118 and is movable from a locked orientation to an unlocked orientation. Preferably, safety lockout 128 is biased away from the locked orientation towards an orientation substantially perpendicular to the longitudinal axis of cartridge body 118. Any suitable bias member may be utilized such as, for example, spring 144. To overcome the bias towards the perpendicular orientation, safety lockout 128 includes a transverse horizontal surface 128*a* (see FIG. 45) formed on the underside thereof which engages a hook 124*b* formed on the upper edge surface of knife 124. This cooperative engagement serves to retain safety lockout 128 in the locked orientation when safety lockout 128 covers knife 124.

When surgical stapler 100 has been unclamped, as will be described in greater detail further herein, after either partial or complete firing, safety lockout 128 is biased to the perpendicular orientation (see FIG. 50), extending upwardly away from cartridge half-section 112. In this manner, surgical stapler 100 cannot be re-clamped until the partial or completely fired cartridge assembly 116 is removed and replaced with a new cartridge assembly 116. Safety lockout 128 also provides a cut-out grasping surface 128*b* with which cartridge assembly 116 may readily be removed from surgical stapler 100.

As previously noted, shipping wedge 130 is removably attachable to cartridge body 118. When installed on cartridge assembly 116, shipping wedge 130 covers the entire surface area of the staple rows 126 and knife track 134. Shipping wedge 130 includes a post 130*b* extending downwardly from the underside near the proximal end thereof. Post 130*b* fits into a complementary shaped opening 118*c* formed in cartridge body 118 at the proximal end of knife track 134. With shipping wedge 130 in place, post 130*b* blocks potential distal movement of knife 126. Post 130*b* maintains knife 134 retained within safety lockout 128 thereby ensuring that the sharpened distal edge 124*a* of knife 124 is covered. Once again, cartridge assembly 116 may be provided without a knife in applications where it is desirable to perform stapling without transection. In such an embodiment, knife 126 is replaced with a blank element to substitute for the knife to interact with safety lockout 128.

Cartridge body 118 includes a series of finger grips 127 formed along the upper sides of the body 118 near a proximal end thereof. The finger grips 127 assist the user in gripping the cartridge assembly 116 for both installation and removal of the cartridge assembly 116 from the cartridge half-section 112. Cartridge body 118 also includes a pair of resilient friction fingers 129 disposed on either side near a proximal end thereof. Friction fingers 129 are configured and adapted to project outwardly from the cartridge body 118 and to frictionally engage the inner surface of the cartridge half-section 112. In this manner, the friction fingers 129 prevent the cartridge assembly 116 from falling out of the cartridge half-section 112.

Referring to FIGS. 35–40, a loading and lockout mechanism for cartridge assembly 116 will now be described in detail. The loading and lockout mechanism facilitates loading of cartridge assembly 116 and prevents firing of surgical stapler 100 until cartridge assembly 116 is properly loaded on cartridge half-section 112 and surgical stapler 100 is properly clamped shut. The loading and lockout mechanism includes a rocker 152 which is pivotally mounted to a channel frame 112*a* (see FIG. 43) of cartridge half-section 112 by way of transversely extending post portions 152*a* seating in openings formed through the sidewalls of channel frame 112*a*. Post portions 152*a* are provided with angled downwardly oriented surfaces to facilitate assembly of rocker 152 with channel frame 112a. Rocker 152 is preferably a molded plastic component and is provided with three slots, namely an open bottomed slots 152b, 152c to permit longitudinal movement of cam bar channel 140 and a closed slot 152d to permit passage of a center bar 154.

Figure 37:
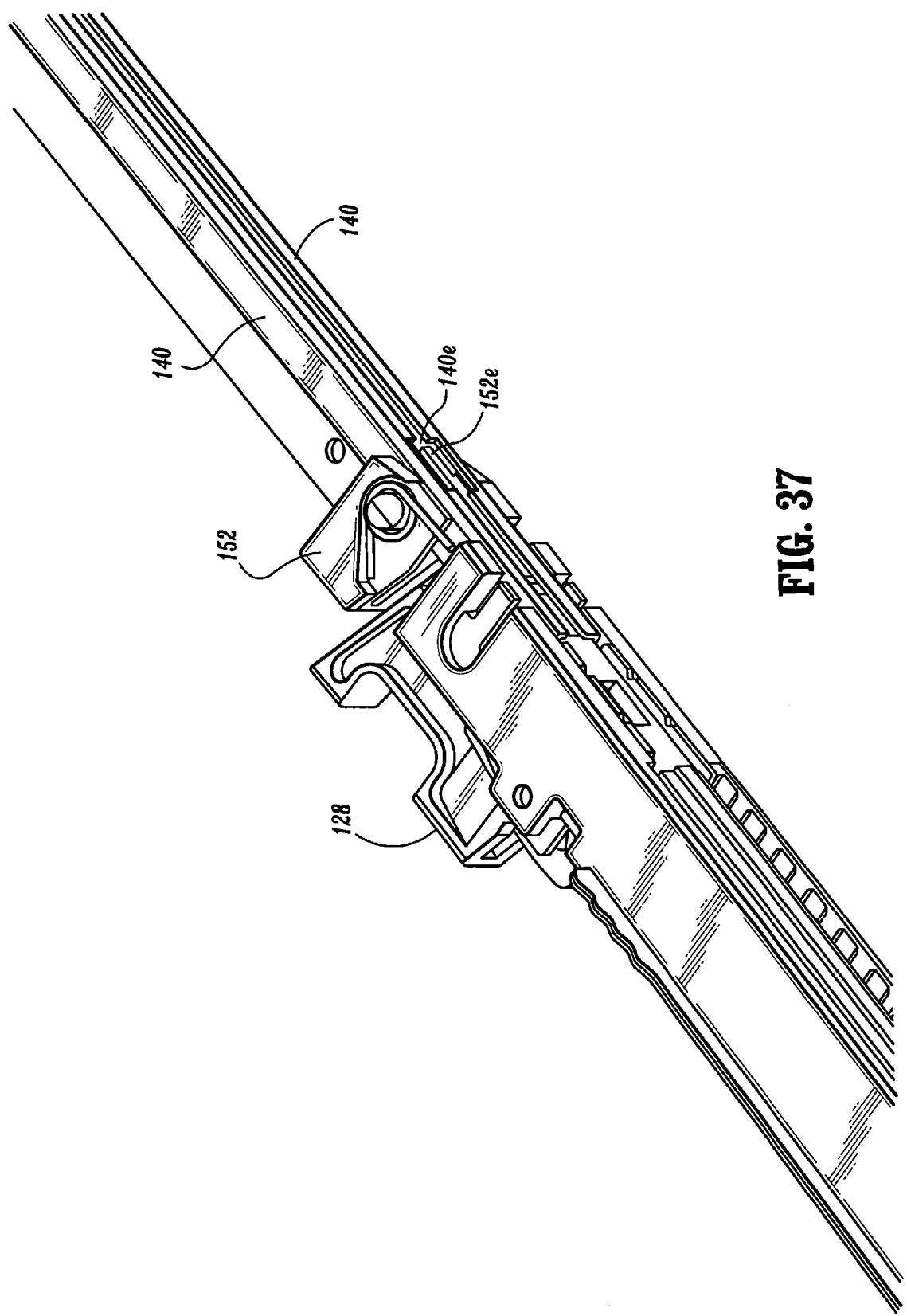
FIG. 37 is an enlarged perspective view, as seen from the bottom of the loading and lock out mechanism, according to the alternative embodiment of the present invention, with a staple cartridge in place thereon.
Figure 38:
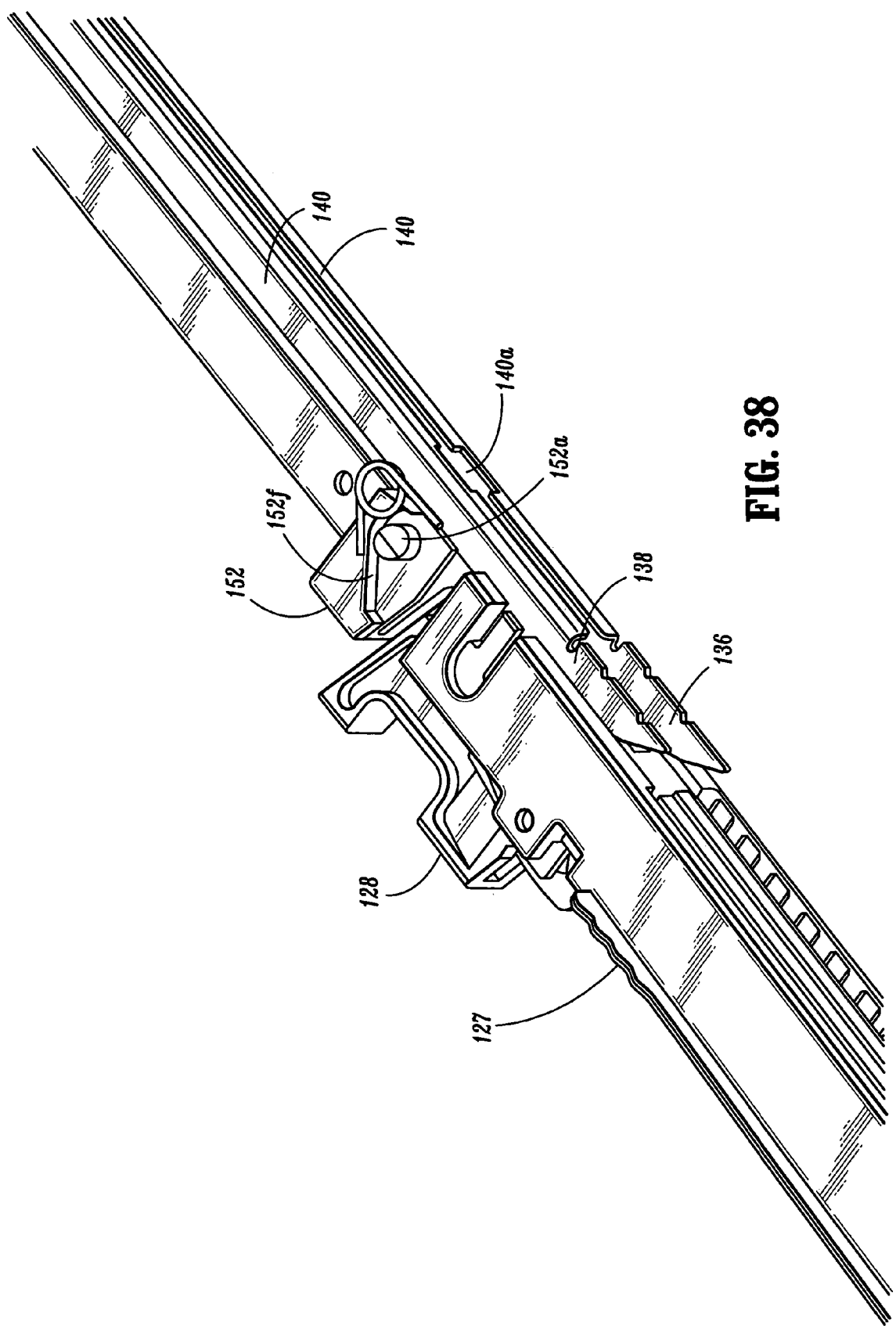
FIG. 38 is a partially exploded enlarged perspective view, as seen from the bottom of the loading and lock out mechanism shown in FIG. 38.
Figure 39:
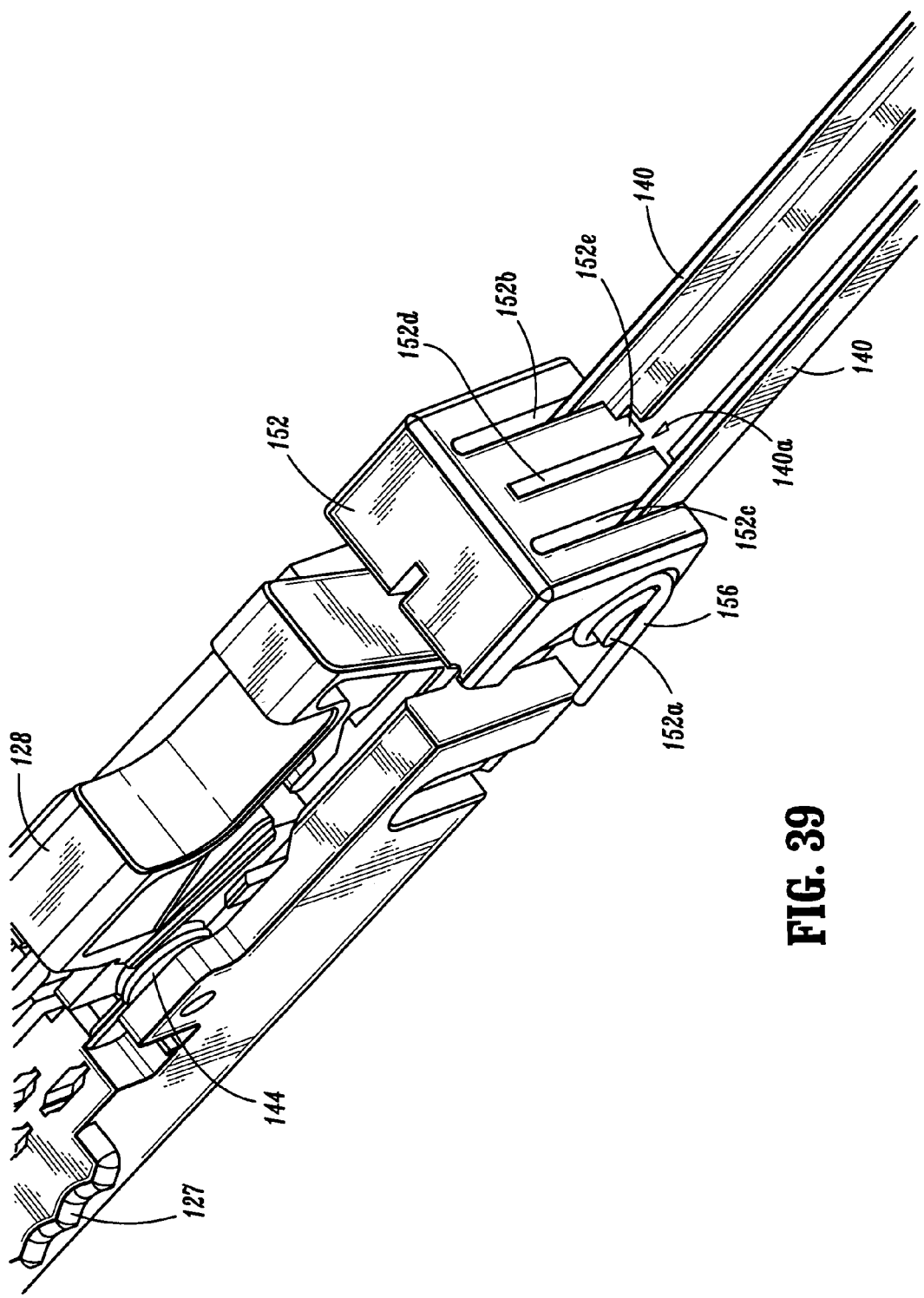
FIG. 39 is an enlarged perspective view similar to FIG. 36, with a staple cartridge in place.
Figure 40:
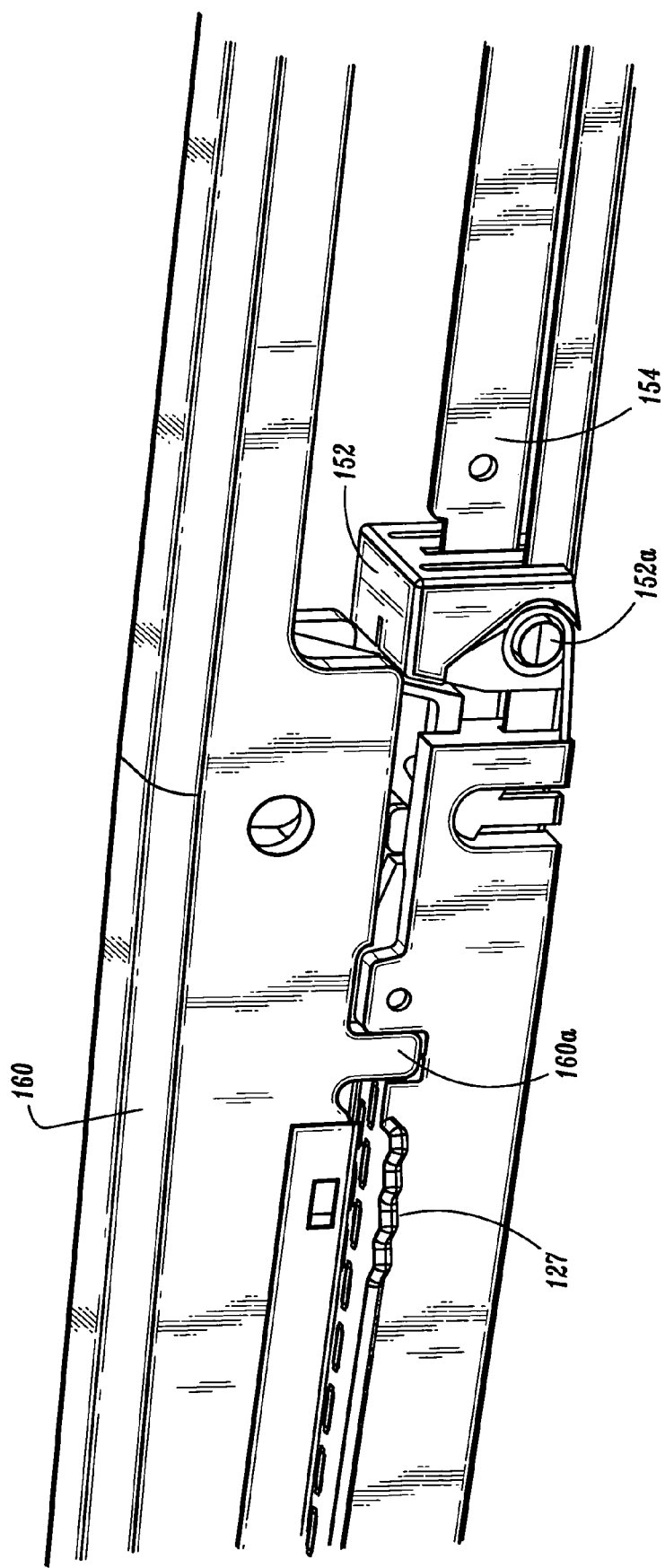
FIG. 40 is an enlarged side perspective view which shows the relative positioning of the loading and lockout mechanism with a staple cartridge installed and with an anvil half-section in place in a clamped condition.

As best shown in FIGS. 37 and 39, rocker 152 is further provided with a downwardly extending blocking surface 152e which is in vertical alignment with an opening 140a formed through the bottom surface of each cam bar 140 when each cam bar 140 is in its proximal-most position. Rocker 152 is biased, by way of a spring 156 which is disposed on transversely extending post portion 152a and between a ridge 152f formed on a side of the rocker 152 and upper surface of the cartridge half section 112 (see FIG. 35), toward a locked-out position wherein blocking surface 152e extends through opening 140a In this manner, each cam bar 140 is prevented from distal longitudinal movement.

Upon loading cartridge assembly 116 on cartridge half-section 112 as shown in FIGS. 37–40 and, the spring bias maintains rocker 152 in the locked-out position. It is only when anvil half-section 114 is joined with cartridge half-section 112 and the half-sections clamped together thereby causing downwardly extending leg portions 160a formed on either side of anvil half-section channel member 160 to bias against cartridge assembly 116, that rocker 152 is urged to rotate by the camming action of proximal end surface of cartridge assembly 116 against the distal end surface of rocker 152. In this manner, blocking surface 152e is moved out of longitudinal alignment with opening 140a of each cam bar 140 thereby permitting distal longitudinal movement thereof.

Similar to the first embodiment, once surgical stapler 100 has been at least partially fired, if the instrument is opened, safety lockout 128 of cartridge assembly 116 automatically moves to the perpendicular orientation due to the spring bias mounting thereof. In this orientation, surgical stapler 100 cannot be re-clamped. Thus, if the user desires to apply further staples, fired or partially fired cartridge assemblies 116 must first be removed and replaced with a non-fired cartridge assembly 116.

Figure 41:
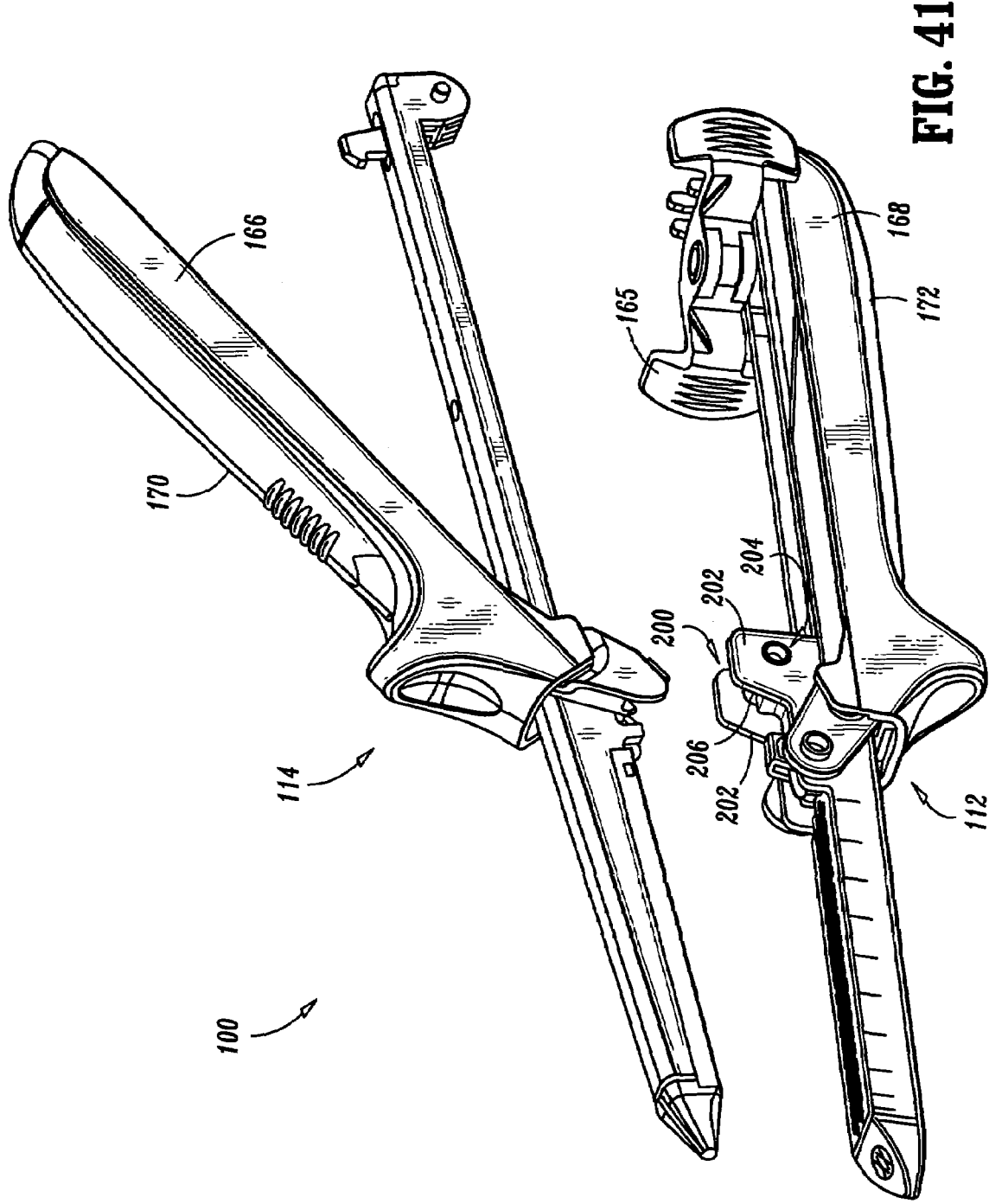
FIG. 41 is a perspective view of the surgical stapler apparatus opened from an anvil half-section side with an anvil half-section clamp lever opened and a cartridge half-section clamp lever closed.
Figure 42:
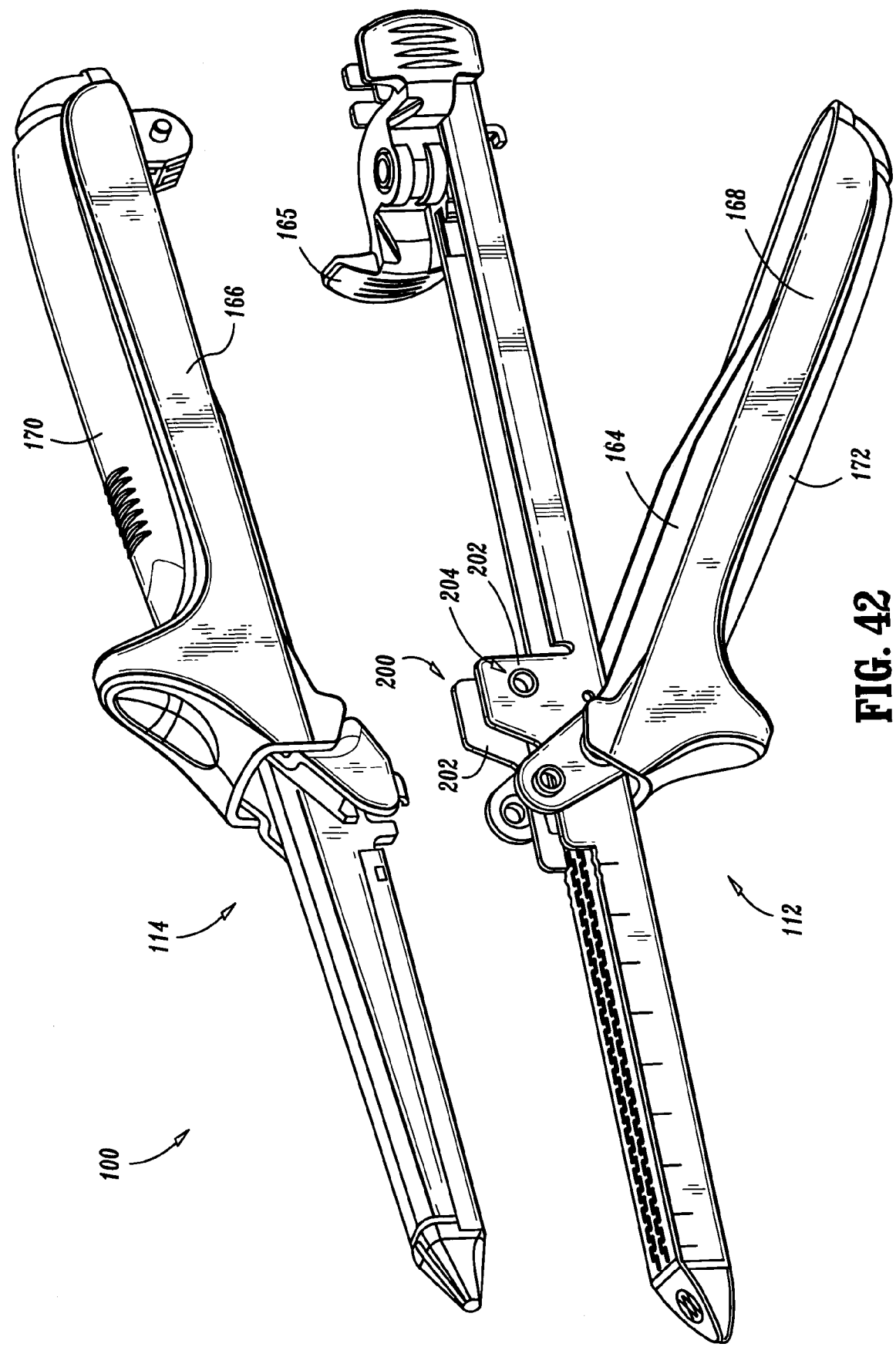
FIG. 42 is a perspective view of the surgical stapler apparatus opened from a cartridge half-section side with a cartridge half-section clamp lever opened and an anvil half-section clamp lever closed.

Referring to FIGS. 41 and 42, surgical stapler 100 is provided with dual selectable clamping levers 162 and 164 and a pivotably mounted firing lever 165. Like clamping levers 62 and 64 of the first embodiment, clamping levers 162 and 164 of the present embodiment provide the user with the uniquely novel option of opening surgical stapler 100 from either half-section 112 or 114. Additionally, firing lever 165 provides the user with the ability to fire surgical stapler 100 from either the left or right side.

Figure 51:
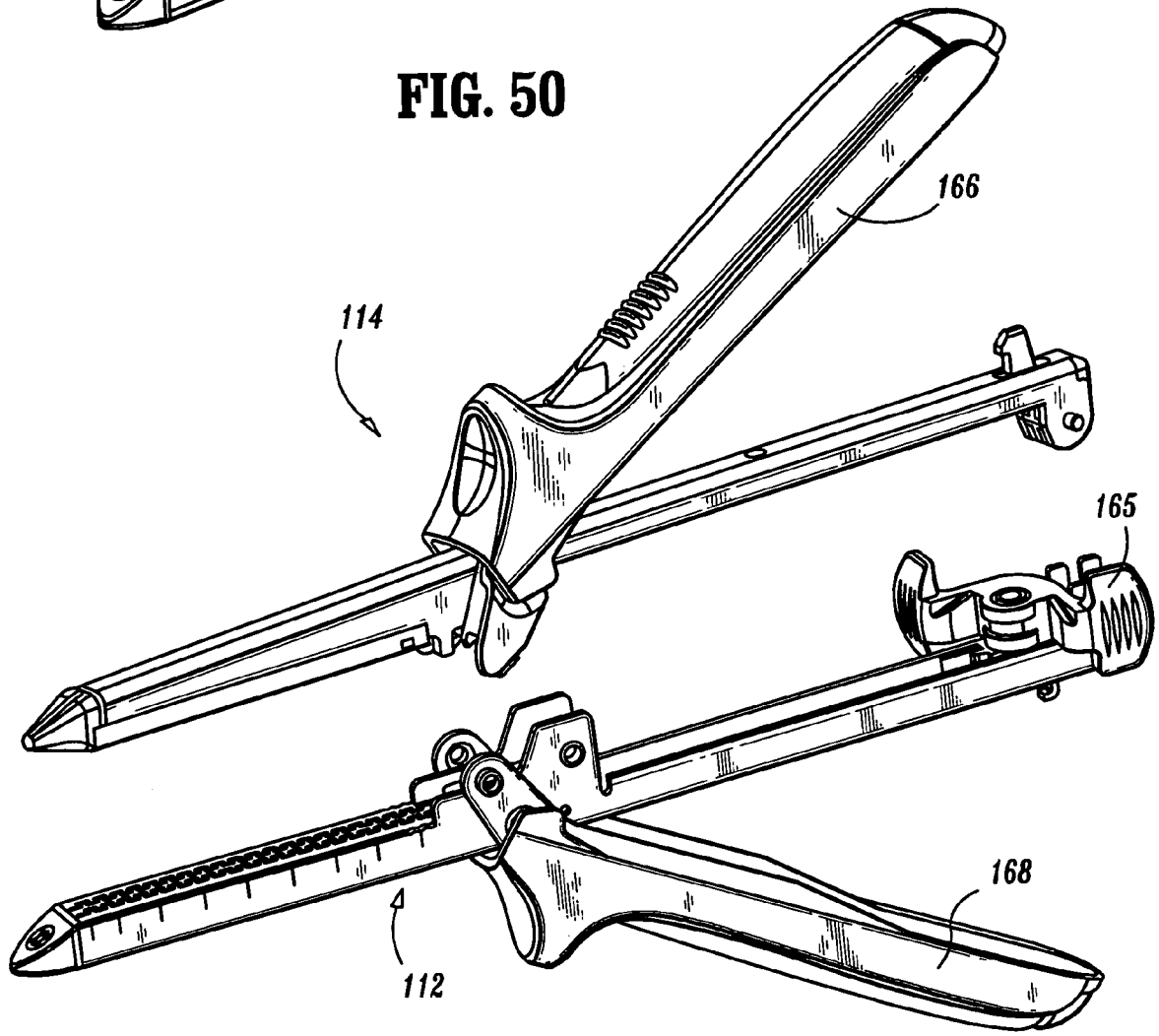
FIG. 51 is a perspective view of the surgical stapler apparatus opened from both the cartridge half-section side with the cartridge half-section clamp lever opened and from the anvil half-section side with the anvil half-section clamp lever opened.

Clamping levers 162 and 164 are pivotably mounted to cartridge half-section 112 and anvil half-section 114, respectively. Clamping levers 162 and 164 provide the user with the ability to open the surgical stapler from either the anvil half-section 114, as seen in FIG. 41, the cartridge half-section 112, as seen in FIG. 42, or simultaneously from both the cartridge half-section 112 and the anvil half-section 114, as seen in FIG. 51. A pair of ergonomic contoured handles 166 and 168 are secured to clamping levers 162 and 164, respectively to provide the user with a convenient gripping handle. To further enhance the gripping of surgical stapler 100 by the user, a pair of friction enhancing inserts 170 and 172 are secured to handles 166 and 168.

Unlike the first embodiment, the surgical stapler 100 according to the alternative embodiment does not have a safety interlock mechanism. In this manner, the user can open the surgical stapler 100 after a complete or partial firing of the cartridge assembly 116. Referring now to FIGS. 43–49, a clamp latch mechanism, according to the alternative embodiment, is provided at the proximal end of surgical stapler 100 which serves to retain clamp levers 162 and 164 in a clamped orientation. Each half section 112 and 114 is provided with a clamp latch mechanism which is essentially the same and which works to latch clamp levers 162 and 164 in a clamped configuration upon squeezing the clamp levers 162 and 164 to the closed position. Accordingly, the following description of the various components which make up the clamp latch mechanism will be directed to that for the cartridge half-section 112.

Figure 43:
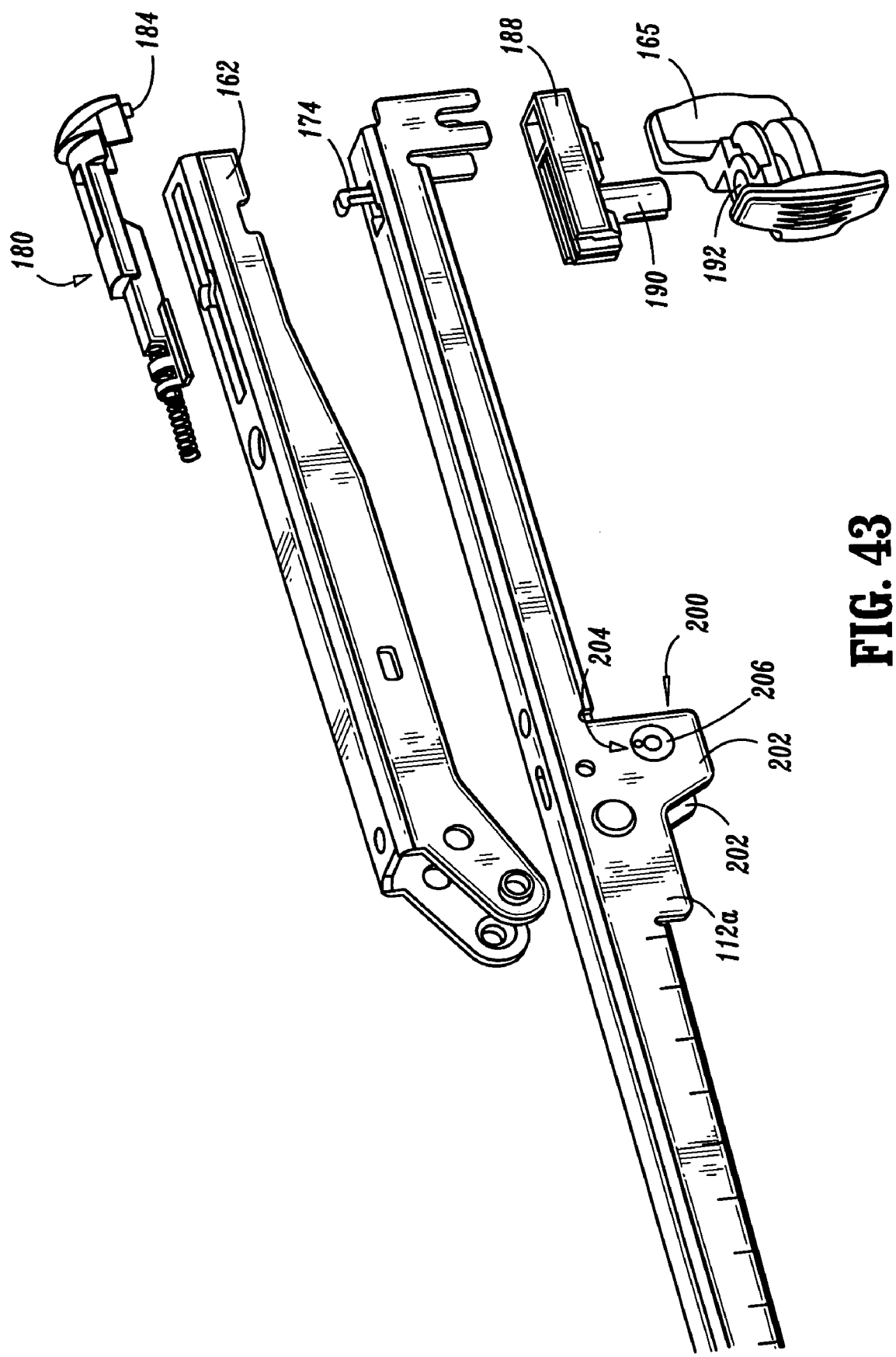
FIG. 43 is a perspective view with parts separated which shows the structural relationship of the various components of a clamp lever lockout and safety interlock mechanism.
Figure 44:
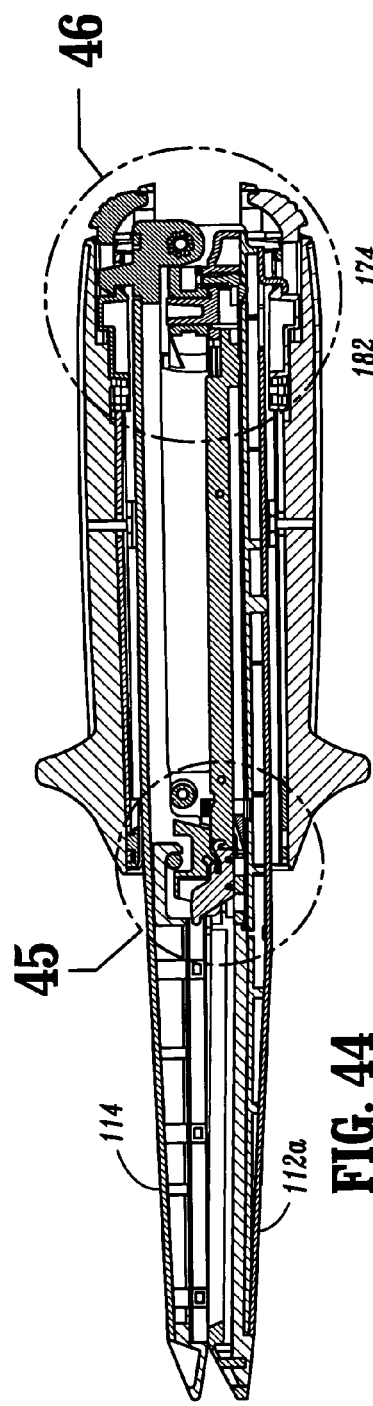
FIG. 44 is a cross-sectional view of the surgical stapler taken along the longitudinal center line thereof.
Figure 46:
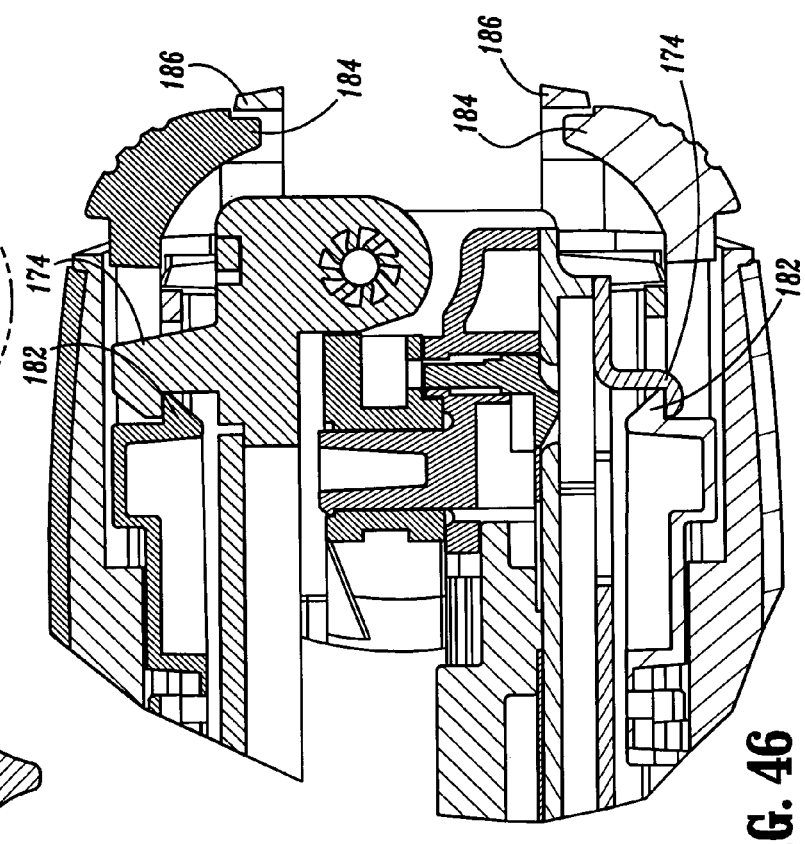
FIG. 46 is an enlarged view of the indicated area of detail of FIG. 44.
Figure 45:
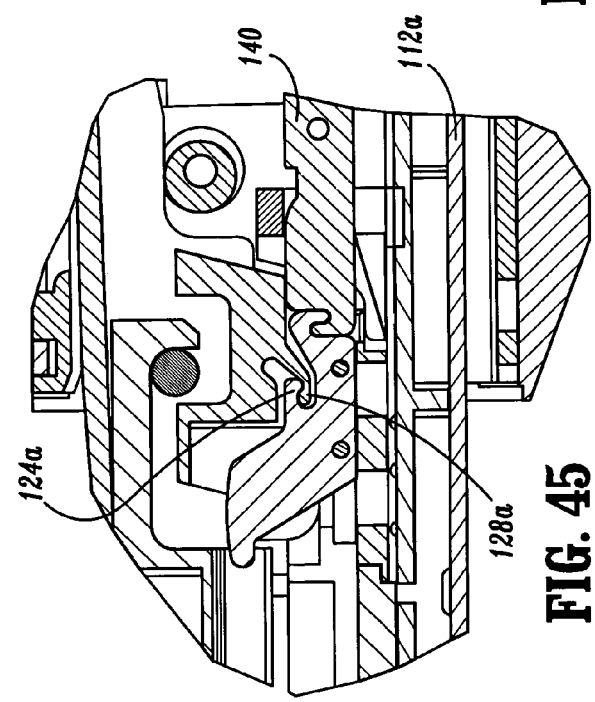
FIG. 45 is an enlarged view of the indicated area of detail of FIG. 44.
Figure 50:
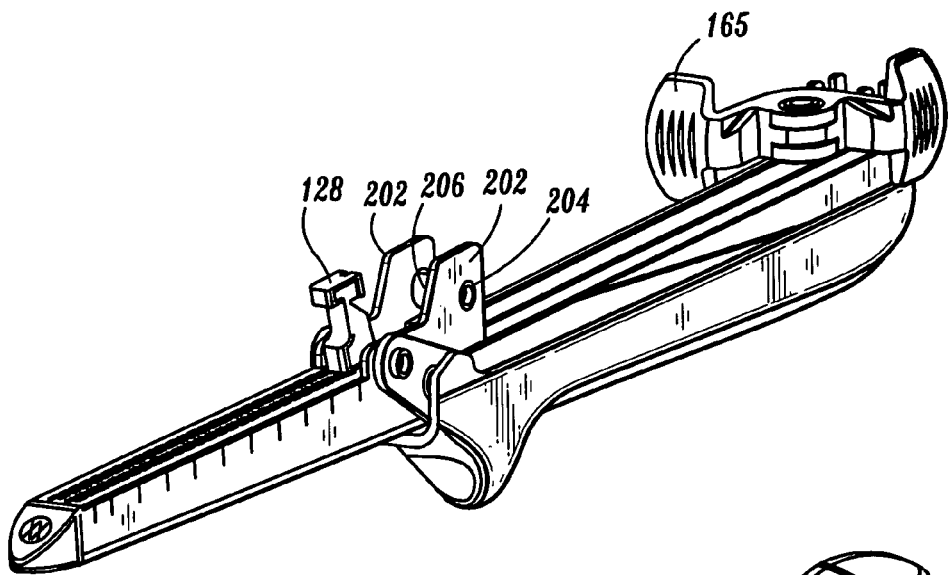
FIG. 50 is a perspective view of the cartridge half-section of the surgical stapler apparatus after partial or complete firing with a staple cartridge safety lockout in a locked out position.

As shown in FIG. 43, the clamp latch mechanism includes a distal clamp lever latch 174 formed at a proximal end of the cartridge half-section 112 and latch handle release member 180 operatively coupled to a proximal end of clamp lever 162. Latch handle release member 180 is spring biased proximally toward a latched position and is provided with a catch 182 for engaging clamp lever latch 174. In order to release clamp lever 162, the user presses release member 180 in the distal direction, thereby disengaging catch 182 from latch 174.

In order to prevent inadvertent opening of the clamp lever 162, release member 180 is provided with a projection 184 extending downwardly from a proximal end thereof, which projection 184 is seated within a guard 186 formed at the proximal end of the lever 162. It is envisioned that the guard 186 can be integral with the handles 166 and 168 and made of a resilient material to enable the user to more easily move the guard 186 and thereby depress the release member 180.

Further, as seen in FIG. 43, surgical stapler 100 is provided with a firing lever slide block 188. Slide block 188 includes a hub 190 projecting therefrom and configured and adapted to be received in a pivot hole 192 formed in firing lever 165. Slide block 188 is configured and adapted to be slidably received in either the cartridge half-section 112 or the anvil half-section 114. In use, the firing lever 165 is pivotable about hub 190 thereby providing the user with the ability to manipulate the firing lever 165 from either side of the surgical stapler 100.

As seen in FIGS. 41–43 and 50, surgical stapler 100 is provided with a staple gap adjustment mechanism 200 which enables each stapler 100 to be manufactured and assembled with a very precise staple gap between the cartridge assembly and the anvil structure of the surgical stapler. The staple gap adjustment mechanism 200 is the subject of commonly owned and U.S. application Ser. No. 10/490,517, filed on Mar. 23, 2004, now U.S. Pat. No. 7,032,799, the entire contents of which are incorporated herein by reference. According to the present embodiment, gap adjustment mechanism 200 includes a pair of upstanding hinge plates 202 formed along the sides of the cartridge half-section 112 and an eccentric cam 206. Each binge plate 202 is provided with a coaxial through hole 204 formed therein and is configured and adapted to receive the eccentric cam 206 therein. In use, as the eccentric cam 206 is rotated, the eccentric cam 206 presses against the anvil half-section 114 until the desired staple gap between the anvil half-section 114 and the cartridge half section 112 is achieved. At which point the eccentric earn 206 is fixedly secured in the through holes 204.

It will be understood that various modifications may be made to the embodiments of the surgical fastener applying apparatus disclosed herein. Therefore, the above description should not be construed as limiting, but merely as exemplifications of preferred embodiments. Those skilled in the art will envision other modifications within the scope and spirit of the present disclosure.

What is claimed:

1. A staple cartridge assembly receivable in a distal end portion of a cartridge receiving half-section of a surgical stapler, the staple cartridge assembly comprising:
   a safety lockout pivotably disposed along an upper surface of the cartridge assembly and movable from an unblocked orientation permitting assembly of an anvil half-section to the cartridge receiving half-section, to a locked orientation preventing assembly of the anvil half-section with the cartridge receiving half section; and
   a loading and lockout mechanism configured and adapted to facilitate loading of the cartridge assembly to the cartridge receiving half-section and to prevent firing of the surgical fastener applying apparatus until the cartridge assembly is properly assembled with cartridge receiving half-section, the loading and lockout mechanism including;
   a rocker pivotably mounted to the cartridge receiving half-section, the rocker having a locked-out position which prevents firing of the surgical fastener applying apparatus and a firing position which permits firing of the surgical fastener applying apparatus, defining a downwardly extending blocking surface, the rocker, when in the locked-out position, engages a cam bar and prevents displacement of the cam bar in a distal direction and, when in the firing position, disengages the cam bar and allows the cam bar to be displaced distally.

2. The stapler cartridge assembly according to claim 1, wherein the safety lockout is biased from the unlocked orientation to the locked orientation.

3. The staple cartridge assembly according to claim 2, wherein the safety lockout is biased by a spring.

4. The staple cartridge assembly according to claim 1, wherein the safety lockout includes a transverse horizontal surface formed on the underside thereof and which is configured and adapted to engage a member formed on a surface of a knife.

5. The staple cartridge assembly according to claim 4, wherein the transverse horizontal surface and the member of the knife are configured and dimensioned such that when the knife is displaced in a distal direction, the member of the knife disengages from the transverse horizontal surface.

6. The staple cartridge assembly according to claim 4, wherein the member of the knife is a hook.

7. The staple cartridge assembly according to claim 1, wherein:
   a) the rocker defines an upper edge blocking surface; and
   b) when the rocker is in the locked-out position, the upper edge blocking surface engages a knife actuating bar and prevents displacement of the knife actuating bar in a distal direction, and, when the rocker is in the firing position, the upper edge blocking surface disengages the knife actuating bar and allows the knife actuating bar to be displaced distally.

8. The staple cartridge assembly according to claim 7, wherein the rocker is biased to the locked-out position.

9. The staple cartridge assembly according to claim 8, wherein the rocker is adapted to be pivoted to the firing position when the anvil half-section is coupled to the cartridge receiving half-section.

10. The staple cartridge assembly according to claim 1, wherein the staple cartridge assembly includes a series of finger grips formed along an upper side surface near a proximal end thereof.

* * * * *